US007556778B2

(12) United States Patent
Kawahara et al.

(10) Patent No.: US 7,556,778 B2

(45) Date of Patent: Jul. 7, 2009

(54) FLUID HANDLING APPARATUS AND FLUID HANDLING UNIT FOR USE THEREIN

(75) Inventors: Noriyuki Kawahara, Saitama (JP); Takuhito Ohse, Saitama (JP)

(73) Assignee: Enplas Corporation, Saitama (JP)

(*) Notice: Subject to any disclaimer, the term of this patent is extended or adjusted under 35 U.S.C. 154(b) by 126 days.

(21) Appl. No.: 11/439,306

(22) Filed: May 22, 2006

(65) Prior Publication Data

US 2006/0266969 A1 Nov. 30, 2006

(30) Foreign Application Priority Data

| | | | |
|---|---|---|---|
| May 25, 2000 | (JP) | ............................. | 2005-151798 |
| Jul. 4, 2005 | (JP) | ............................. | 2005-195334 |
| Aug. 11, 2005 | (JP) | ............................. | 2005-232837 |

(51) Int. Cl.
*B01L 3/00* (2006.01)
*C12M 1/16* (2006.01)

(52) U.S. Cl. ......................... 422/102; 422/99; 422/100; 435/287.1; 435/288.4; 435/288.5

(58) Field of Classification Search ....................... None
See application file for complete search history.

(56) References Cited

U.S. PATENT DOCUMENTS

| | | | | |
|---|---|---|---|---|
| 5,108,704 | A * | 4/1992 | Bowers et al. | 422/70 |
| 6,054,325 | A * | 4/2000 | Kedar et al. | 436/178 |
| 2002/0106310 | A1* | 8/2002 | Zuk, Jr. | 422/102 |
| 2003/0064423 | A1* | 4/2003 | Gordon et al. | 435/7.92 |
| 2003/0170147 | A1* | 9/2003 | Voegelin et al. | 422/101 |
| 2005/0136546 | A1* | 6/2005 | Berndt et al. | 436/45 |
| 2007/0111304 | A1* | 5/2007 | Ohse et al. | 435/287.2 |
| 2007/0181507 | A1* | 8/2007 | Ohse | 210/744 |
| 2007/0217955 | A1* | 9/2007 | Kawahara et al. | 422/99 |

FOREIGN PATENT DOCUMENTS

| | | |
|---|---|---|
| JP | 9-101302 | 4/1997 |
| JP | 9-159673 | 6/1997 |
| JP | 2001-4628 | 1/2001 |

* cited by examiner

*Primary Examiner*—Jill Warden
*Assistant Examiner*—P. Kathryn Wright
(74) *Attorney, Agent, or Firm*—Bachman & Lapointe, P.C.

(57) ABSTRACT

A fluid handling apparatus 10includes a plurality of fluid handling subassemblies 16, each of which is mounted in a corresponding one of mounting recessed portions 14 of a plate body 12. Each of the fluid handling subassemblies 16 has an injecting section 26 for injecting a fluid, a fluidized section 28 for receiving the fluid from the injecting section 26 to allow the fluid to continuously flow downwards, a fluid housing chamber 30 for receiving the fluid from the fluidized section 28, a fluid passage for allowing the fluid, which reaches the bottom of the fluidized section 28, to enter the fluid housing chamber 30, and a plurality of disks 22 (a large number of beads 122, or a water absorptive member 222) arranged in the fluidized section.

12 Claims, 28 Drawing Sheets

FLUID HANDLING APPARATUS AND FLUID HANDLING UNIT FOR USE THEREIN

BACKGROUND OF THE INVENTION

1. Field of the Invention

The present invention generally relates to a fluid handling apparatus and a fluid handling unit for use therein. More specifically, the invention relates to a fluid handling apparatus capable of being used as a sample analyzing apparatus for analyzing samples, such as biosubstances representative of functional substances, and a fluid handling unit for use therein.

2. Description of the Prior Art

As conventional methods for specifically detecting biosubstances, such as proteins, there are known various methods for causing an antigen-antibody reaction using an antibody to a specific biosubstance, to carry out the visual recognition or spectroscopic measurement of a reactant thus obtained, to detect the biosubstance.

As methods for quantifying a reactant obtained by an antigen-antibody reaction of a biosubstance, such as a protein, there are widely adopted some methods, such as ELISA (Enzyme-Linked ImmunoSorbent Assay). In these methods, there is used a sample analyzing apparatus called a microplate wherein a large number of fine recessed portions generally called microwells (which will be hereinafter referred to as "wells") are arrayed. The wall surfaces of the wells are coated with an antibody to a specific biosubstance, which is a target substance, as a capturing (or catching) material, to capture (or catch) the target substance by the capturing material to detect the target substance by measuring a reactant, which is obtained by an antigen-antibody reaction between the target substance and the antibody, by fluorescence, luminous reagents or the like.

In a typical method using a microplate, such as ELISA, the absorbance or fluorescence of a liquid obtained by an antigen-antibody reaction is measured. In this case, a value obtained by optical measurement depends on the quantity of the liquid if the liquid is a dilute solution. That is, the value obtained by optical measurement is in proportional to the height of the liquid, which is filled in a well, from the bottom of the well to the liquid level. For example, when fluorescence is measured, the intensity of fluorescence F is in proportion to the length of layer L, so that it is in proportion to the quantity of the liquid which is fed into the well, as described in the following expression.

$$F = kI_0 fecL$$

(k: Proportional Coefficient, $I_0$: Intensity of Excitation Light, f: Quantum Convergence of Fluorescence, e: Molar Absorption Coefficient at Wavelength of Excitation Light, c: Concentration of Fluorescent Material, L: Length of Layer)

Particularly in a typical ELISA based on the measurement of fluorescence, after a target substance is captured by a capturing antibody coated on a wall surface of the well, a detecting antibody bonded to oxygen is fed into the well, and a substrate is finally fed into the well to measure fluorescence due to an enzyme reaction of the substrate. Therefore, the quantity of a fluorescent material produced by an enzyme reaction in a predetermined period of time is determined by the quantity of the captured target substance, so that the concentration of the fluorescent material depends on the quantity of the liquid which is fed into the well. That is, if the quantity of the liquid fed into the well is increased, the concentration of the fluorescent material produced in the predetermined period of time is decreased. Therefore, if the quantity of the liquid fed into the well is increased in order to enhance the sensitivity of measurement, the length of layer L in the above described expression is increased, but the concentration c of the fluorescent material is decreased, so that it is not possible to sufficiently improve the sensitivity of measurement.

Thus, in the conventional method using the microplate, such as ELISA, the antigen-antibody reaction proceeds only on the wall surface of the well coated with the capturing antibody. Therefore, the liquid must be allowed to stand until the reaction occurs after the target substance, antibody and substrate contained in the liquid fed into the well are suspended, circulated and sink to reach the wall surface of the well, so that there is a problem in that the efficiency of reaction is bad. In addition, since the microplate is subdivided into a large number of wells, the quantity of a liquid fed into each of the wells is limited, so that there is a problem in that the sensitivity of measurement is deteriorated. Moreover, in order to increase the height of the liquid, which is filled in each of the wells, from the bottom of the well to the liquid level to prevent the deterioration of the sensitivity of measurement, it is required to increase the quantity of samples and reagents to be used, so that costs are increased.

There is known a method using a porous material as a capturing material as a method for improving the efficiency of reaction and the sensitivity of measurement. However, it is required to provide an external power, such as a pump, in order to control the flowability of the liquid, and it is difficult to continuously control the flowability of the liquid since the porous material is easily clogged up. There is also known a method for fluidizing a liquid by pressurization or suction as a method using a microchip having a fine space to fluidize a liquid in the fine space. However, it is also required to provide an external power and a complicated device in this method. Moreover, there is known a method using a microchip having a fine space to fluidize a liquid in the fine space by a valve structure. However, it is also required to provide power or energy for operating the valve in this method.

In order to improve the sensitivity of measurement and shorten the measuring time in ELISA or the like, there is proposed a microplate capable of increasing the surface area of a reaction surface (capturing surface) to enhance the sensitivity of measurement by forming fine irregularities on the bottom surface of each of wells serving as the reaction surface (see, e.g., Japanese Patent Laid-Open No. 9-159673). There is also proposed a microchip capable of increasing the surface area of a reaction surface to enhance the efficiency of reaction in a fine space by arranging a fine solid particle (bead) as a reaction solid phase in a microchannel of the microchip (see, e.g., Japanese Patent Laid-Open No. 2001-4628). Moreover, there is proposed a microplate capable of increasing the surface area of a reaction surface and saving the quantity of samples by forming a small-diameter recessed portion in the central portion of the bottom of each of wells. (see, e.g., Japanese Patent Laid-Open No. 9-101302).

However, in the microplate proposed in Japanese Patent Laid-Open No. 9-159673, there is a problem in that it is not possible to improve the efficiency of reaction although it is possible to improve the sensitivity of measurement. In addition, the microchip proposed in Japanese Patent Laid-Open No. 2001-4628 is not suitable for the measurement of a large number of specimens although it is possible to improve the efficiency of reaction since it is a microchip having a microchannel structure, not a microplate typically used in ELISA or the like. Moreover, in the microplate proposed in Japanese Patent Laid-Open No. 9-101302, it is not possible to sufficiently improve the efficiency of reaction and the sensitivity of measurement and to save the quantity of samples and reagents to be used, although it is possible to improve the surface area of the reaction surface to some extent.

SUMMARY OF THE INVENTION

It is therefore an object of the present invention to eliminate the aforementioned problems and to provide a fluid handling apparatus which is capable of improving the efficiency of reaction and the sensitivity of measurement with a simple structure and of shortening a reaction time and a measuring time and which is capable of saving the quantity of samples and reagents to be used to reduce costs, when the apparatus is used as a sample analyzing apparatus for measuring a large number of specimens, and a fluid handling unit for use therein.

In order to accomplish the aforementioned and other objects, according to one aspect of the present invention, a fluid handling apparatus comprises an apparatus body and a plurality of fluid handling subassemblies arranged on the apparatus body, each of the fluid handling subassemblies comprising: an injecting section for injecting a fluid, the injecting section having a bottom which has an opening; a fluidized section for receiving the fluid from the opening of the bottom of the injecting section to allow the fluid to continuously flow downwards; a fluid housing chamber for receiving the fluid from the fluidized section; a fluid passage for allowing the fluid, which reaches a bottom of the fluidized section, to enter the fluid housing chamber; and a surface-area increasing means, arranged in the fluidized section, for increasing a surface area of a contact surface with the fluid in the fluidized section. In this fluid handling apparatus, the apparatus body may comprise a plate member. In this case, a plurality of recessed portions are preferably formed in one surface of the plate member so as to be arrayed, and each of the plurality of fluid handling subassemblies is preferably mounted in a corresponding one of the recessed portions. The apparatus body may comprise a frame and a plurality of supporting members which are arranged on the frame so as to be substantially parallel to each other, each of the supporting members having a plurality of recessed portions which are arranged in a row at regular intervals, and each of the plurality of fluid handling subassemblies being mounted in a corresponding one of the recessed portions. In these fluid handling apparatuses, the fluidized section is preferably arranged so as to surround the fluid housing chamber.

In the above described fluid handling apparatus, the surface-area increasing means preferably comprises a plurality of plate members which are stacked in vertical directions to form spaces between the plate members, and the fluid fed into the fluidized section flows on an upper surface of each of the plate members. Each of the plurality of recessed portions is preferably a substantially circular recessed portion, the fluidized section being formed between an outer cylindrical member, which is inserted into each of the plurality of recessed portions, and an inner cylindrical member which is inserted into the outer cylindrical member, the fluid housing chamber being formed in the inner cylindrical member, the surface-area increasing means comprising a plurality of circular plate members which are stacked so as to surround the inner cylindrical member, the injecting section being formed between an upper cylindrical member, which is arranged over the plurality of circular plate members, and the inner cylindrical member, a space being formed between adjacent two of the plurality of circular plate members, and the fluid fed into the fluidized section moving on an upper surface of each of the circular plate members. In this case, the fluid fed into the fluidized section is preferably allowed to flow on an uppermost circular plate member of the plurality of circular plate members from a peripheral portion of the uppermost circular plate member to the opposite side in radial directions, to flow downwards in vertical directions to reach a peripheral portion of a second circular plate member of the plurality of circular plate members below the uppermost circular plate member, to sequentially flow on each of the plurality of circular plate members to reach a lowermost circular plate member of the plurality of circular plate members.

In the above described fluid handling apparatus, the surface-area increasing means may comprise a large number of fine particles filled in the fluidized section. Each of the plurality of recessed portions may be a substantially circular recessed portion, the fluidized section being formed between an outer cylindrical member, which is inserted into each of the plurality of recessed portions, and an inner cylindrical member which is inserted into the outer cylindrical member, the fluid housing chamber being formed in the inner cylindrical member, the injecting section being formed between an upper cylindrical member, which is arranged over the outer cylindrical member, and the inner cylindrical member, and the surface-area increasing means comprising a large number of fine particles filled in the fluidized section.

In the above described fluid handling apparatus, the surface-area increasing means may be a water absorptive member arranged in the fluidized section. Each of the plurality of recessed portions may be a substantially circular recessed portion, the fluidized section being formed between an outer cylindrical member, which is inserted into each of the plurality of recessed portions, and an inner cylindrical member which is inserted into the outer cylindrical member, the fluid housing chamber being formed in the inner cylindrical member, and the injecting section being formed over a water absorptive member which is arranged as the surface-area increasing means in the fluidized section.

In the above described fluid handling apparatus, each of the plurality of recessed portions may comprise an upper cylindrical recessed portion, and a lower cylindrical recessed portion which is formed in a bottom of the upper recessed portion and which has a smaller diameter than that of the upper recessed portion, the fluidized section being formed between the upper recessed portion and a cylindrical member which is inserted into each of the plurality of recessed portions, the fluid housing chamber being formed in the cylindrical member, and the injecting section being formed over a large number of fine particles which are filled as the surface-area increasing means in the fluidized section.

According to another aspect of the present invention, a fluid handling unit comprises: an injecting section for injecting a fluid, the injection section having a bottom which has an opening; a fluidized section for receiving the fluid from the opening of the bottom of the injecting section to allow the fluid to continuously flow downwards; a fluid housing chamber, formed so as to be surrounded by the fluidized section, for receiving the fluid from the fluidized section; a fluid passage for allowing the fluid, which reaches a bottom of the fluidized section, to enter the fluid housing chamber; and a surface-area increasing means, arranged in the fluidized section, for increasing a surface area of a contact surface with the fluid in the fluidized section.

According to a further aspect of the present invention, a fluid handling unit comprises a supporting member and a plurality of fluid handling subassemblies which are arranged on the supporting member in a row at regular intervals, each of the fluid handling subassemblies comprising: an injecting section for injecting a fluid, the injecting section having a bottom which has an opening; a fluidized section for receiving the fluid from the opening of the bottom of the injecting section to allow the fluid to continuously flow downwards; a fluid housing chamber, formed so as to be surrounded by the fluidized section, for receiving the fluid from the fluidized section; a fluid passage for allowing the fluid, which reaches a bottom of the fluidized section, to enter the fluid housing chamber; and a surface-area increasing means, arranged in the fluidized section, for increasing a surface area of a contact surface with the fluid in the fluidized section.

in these fluid handling units, the fluid housing chamber is preferably surrounded by the fluidized section via a wall portion. The fluidized section is preferably formed between an outer cylindrical member having a bottom, and an inner cylindrical member which is inserted into the outer cylindrical member, the fluid housing chamber being formed in the inner cylindrical member, and the injecting section being formed between an upper cylindrical member, which is arranged over the outer cylindrical member, and the inner cylindrical member. The surface-area increasing means preferably comprises a plurality of plate members which are stacked in vertical directions, a space being formed between adjacent two of the plate members, and the fluid fed into the fluidized section being allowed to flow on each of the plate members. Alternatively, the surface-area increasing means may comprise a large number of fine particles which are filled in the fluidized section, or a water absorptive member which is arranged in the fluidized section.

According to the present invention, it is possible to provide a fluid handling apparatus which is capable of improving the efficiency of reaction and the sensitivity of measurement with a simple structure and of shortening a reaction time and a measuring time and which is capable of saving the quantity of samples and reagents to be used to reduce costs, when the apparatus is used as a sample analyzing apparatus for measuring a large number of specimens, and a fluid handling unit for use therein.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of a fluid handling apparatus and a fluid handling unit for use therein according to the present invention will be described below in detail.

First Preferred Embodiment

Figure 1:
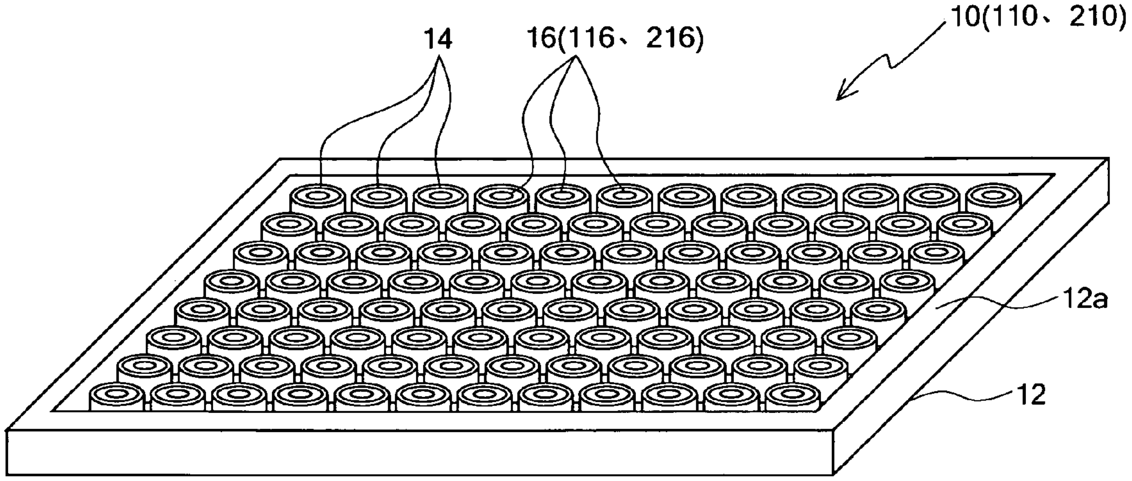
FIG. 1 is a perspective view of the first preferred embodiment of a fluid handling apparatus according to the present invention.

FIGS. 1 through 7 show the first preferred embodiment of a fluid handling apparatus according to the present invention. For example, the fluid handling apparatus 10 in this preferred embodiment can be used as an apparatus for analyzing a sample containing a biosubstance, such as a protein, which is representative of functional substances. In general, the fluid handling apparatus 10 can be used as a sample analyzing apparatus called a microwell plate for carrying out the measurement of a large number of specimens. As shown in FIG. 1, the fluid handling apparatus 10 comprises: a substantially rectangular plate body 12 serving as an apparatus body having a plurality of substantially cylindrical protruding portions (96 protruding portions arrayed as 8×12 in this preferred embodiment), each of which has a substantially cylindrical recessed portion 14 (which will be hereinafter referred to as a "mounting recessed portion 14") generally called a microwell; and a plurality of fluid handling subassemblies 16, each of which serves a fluid handling unit fitted into a corresponding one of the mounting recessed portions 14.

The plate body 12 comprises: a substantially rectangular plate portion which is made of a resin material, such as polycarbonate (PC) or polymethyl methacrylate (PMMA), or a glass material and which has a thickness of a few millimeters, the length of each side of the plate portion being in the range of from a few centimeters to over ten centimeters; a peripheral wall portion 12*a* which protrudes from the peripheral portion of one surface (upper surface) of the plate portion in a substantially vertical direction and which extends along the peripheral portion, the peripheral wall portion 12*a* having a height of a few millimeters; and a plurality of substantially cylindrical protruding portions which are arranged at regular intervals in a portion (a substantially rectangular recessed portion) surrounded by the peripheral wall portion 12*a* and which protrude from the one surface (upper surface) of the plate portion in the substantially vertical direction, each of the protruding portions having a height of a few millimeters and having a substantially cylindrical mounting recessed portion 14. Furthermore, if the plate body 12 has the mounting recessed portions 14, it is not always required to form the above described cylindrical protruding portions. The plate body 12 may be a commercially available microwell plate having a large number of wells (recessed portions) (e.g., 96 wells arrayed as 8×12).

Figure 2:
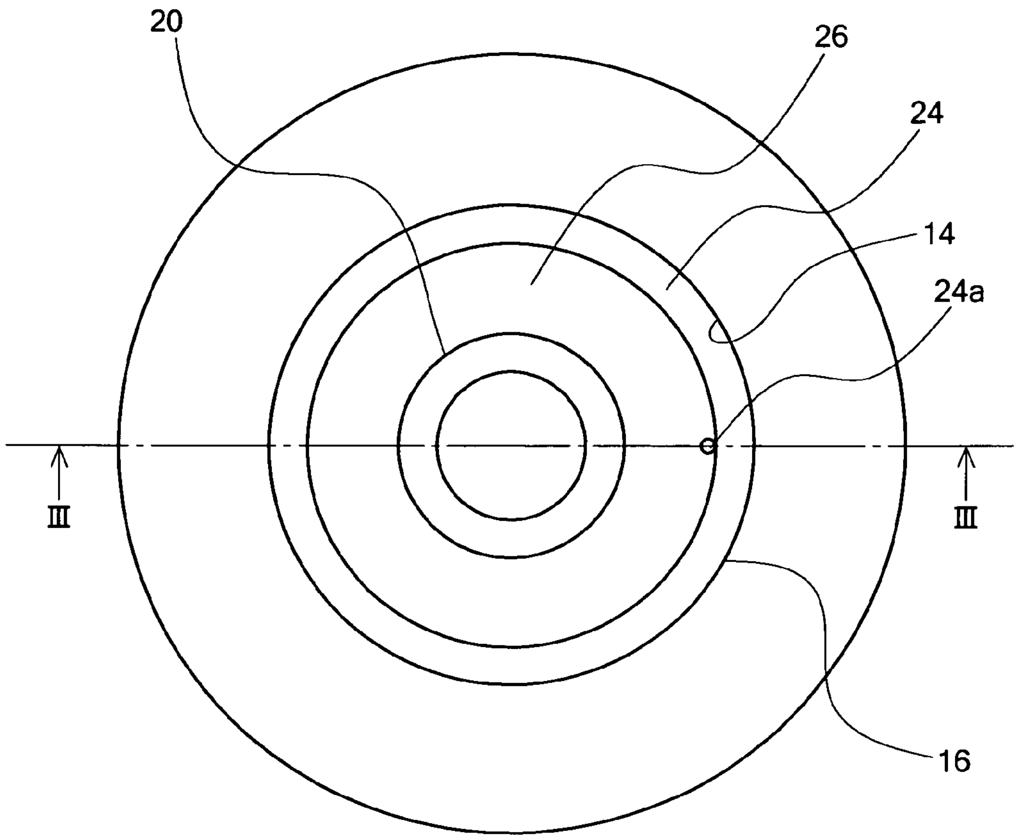
FIG. 2 is an enlarged plan view of a fluid handling subassembly which is mounted in each of mounting recessed portions of the first preferred embodiment of a fluid handling apparatus according to the present invention.
Figure 3:
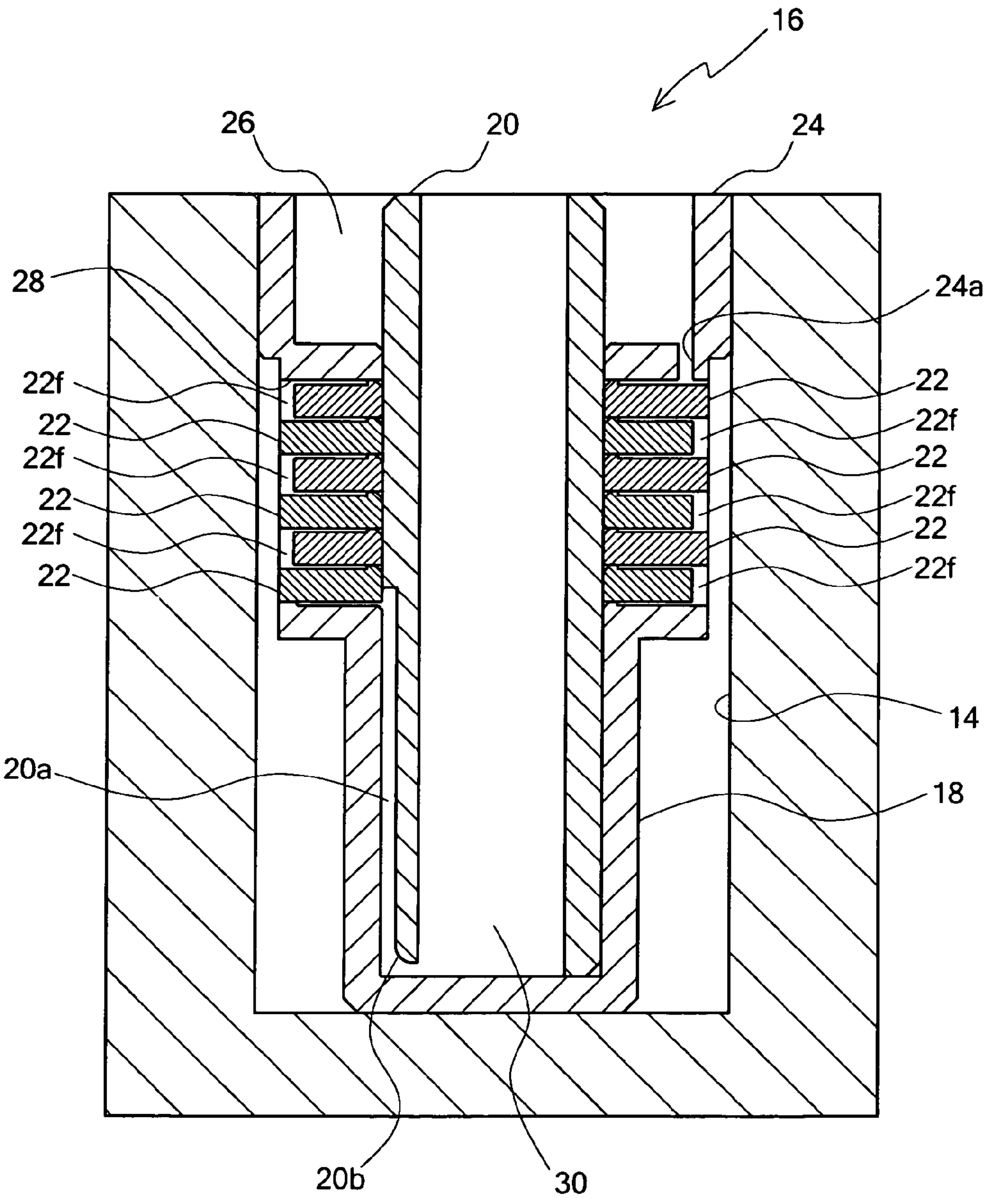
FIG. 3 is a sectional view taken along line III-III of FIG. 2.
Figure 4:
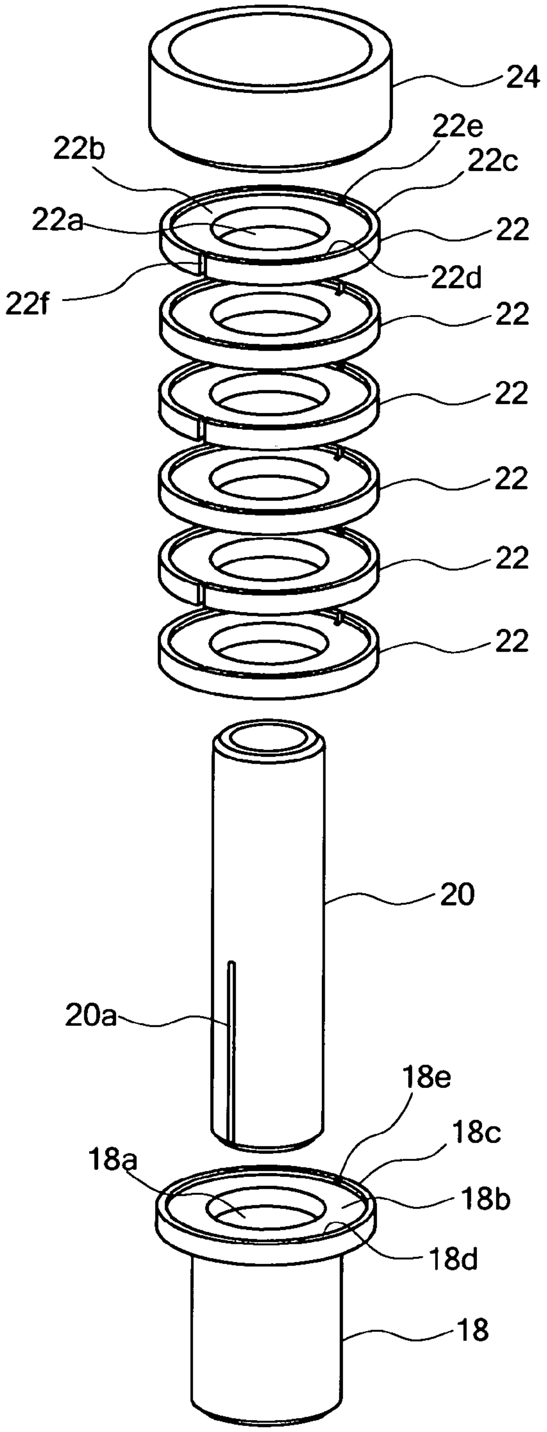
FIG. 4 is an exploded perspective view of the fluid handling subassembly of FIG. 2.
Figure 5:
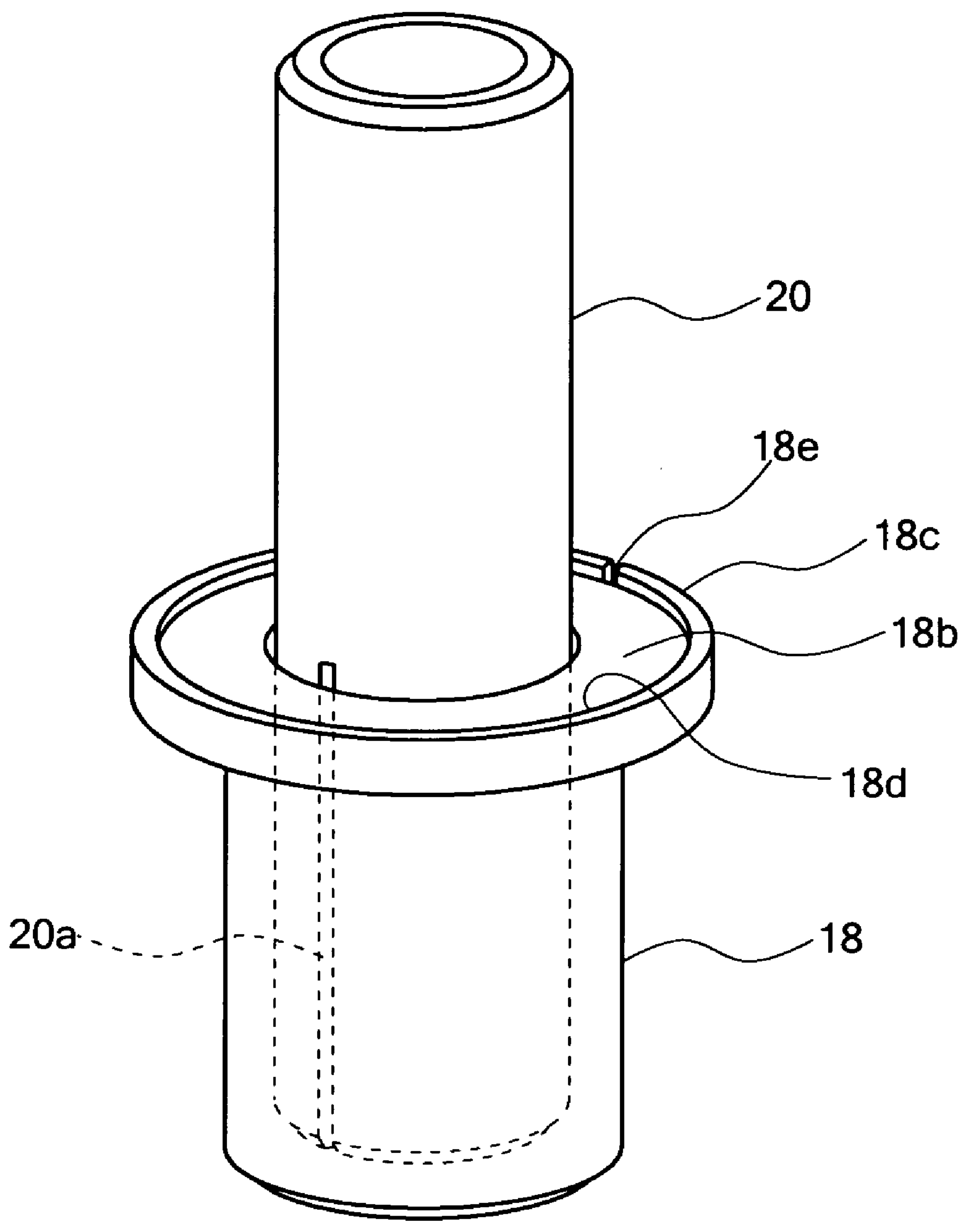
FIG. 5 is a perspective view showing a state that an inner cylindrical member of the fluid handling subassembly of FIG. 2 is inserted into an outer cylindrical member thereof.
Figure 6:
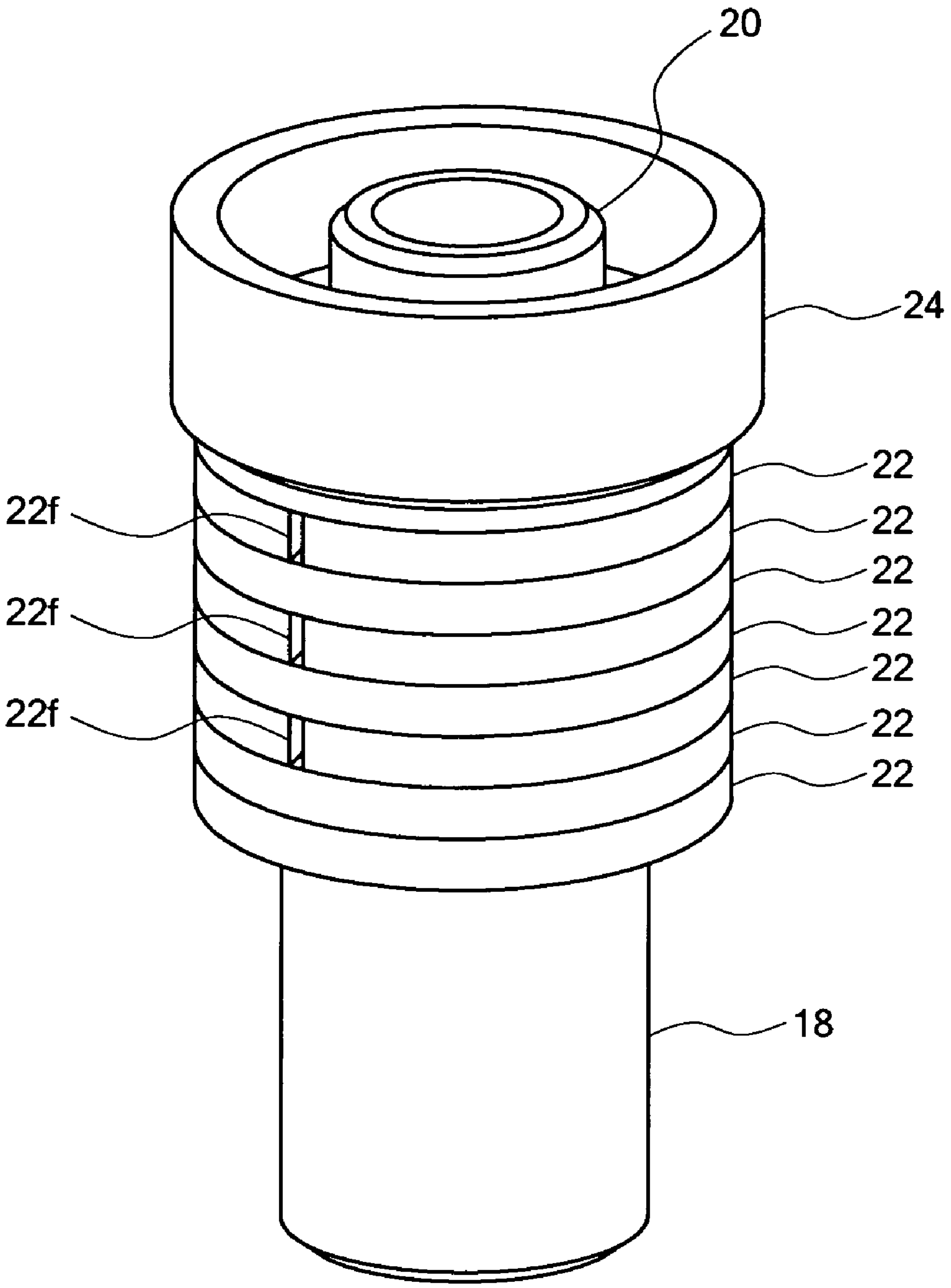
FIG. 6 is a perspective view showing a state the fluid handling subassembly of FIG. 2 is assembled.
Figure 7:
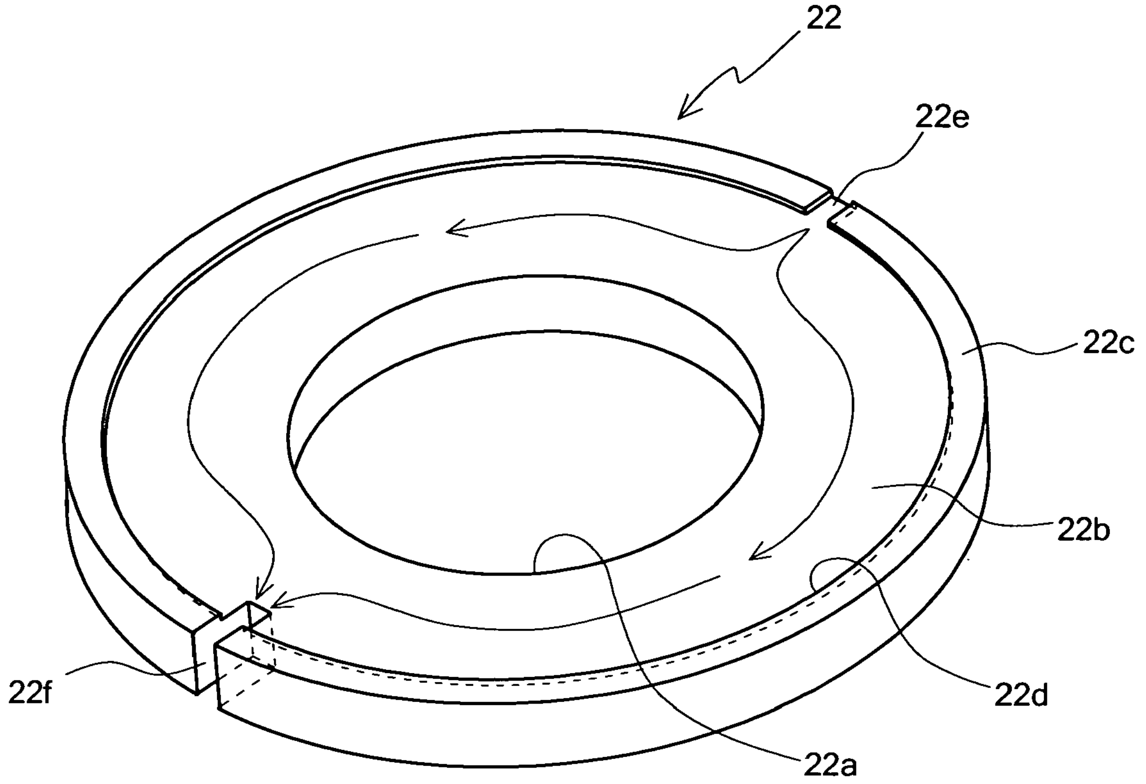
FIG. 7 is a perspective view of a disk (circular plate) of the fluid handling subassembly of FIG. 2.

FIGS. 2 through 6 are enlarged views showing a fluid handling subassembly 16 which is mounted in each of the mounting recessed portions 14 of the fluid handling apparatus 10 in this preferred embodiment. FIG. 2 is a plan view of the fluid handling subassembly 16 which is mounted in each of the mounting recessed portions 14 of the fluid handling apparatus 10, and FIG. 3 is a sectional view taken along line III-III of FIG. 2. FIG. 4 is an exploded perspective view of the fluid handling subassembly 16, FIG. 5 is a perspective view showing a state that an inner cylindrical member 20 of the fluid handling subassembly 16 is inserted into an outer cylindrical member 18 thereof, and FIG. 6 is a perspective view showing a state that the fluid handling subassembly 16 is assembled.

As shown in FIGS. 2 through 6, each of the fluid handling subassemblies 16 comprises an outer cylindrical member 18 having a substantially cylindrical shape, an inner cylindrical member 20 having a substantially cylindrical shape, a plurality of annular disks (circular plates) 22, and a substantially cylindrical lid member 24.

The outer cylindrical member 18 has a substantially cylindrical shape having a diameter and height of a few millimeters. The lower end of the outer cylindrical member 18 is closed by its bottom. Furthermore, it is not always required to close the lower end of the outer cylindrical member 18 by the bottom. The upper end of the outer cylindrical member 18 has a substantially circular opening 18*a*. In addition, an annular flange portion 18*b* protruding from the upper end portion of the outer cylindrical member 18 outwardly in a substantially horizontal direction is formed so as to surround the opening 18*a*. The outside diameter of the flange portion 18*b* is smaller than the inside diameter of the mounting recessed portion 14 (see FIG. 3). The outer periphery of the flange portion 18*b* has an annular wall portion 18*c* which extends in circumferential directions and protrudes upwards in a substantially vertical direction and which has a height of a few micrometers to 100 micrometers, preferably a height of about 50 micrometers. The annular wall portion 18*c* defines an annular recessed portion 18*d* on the upper surface of the flange portion 18*b*. The annular wall portion 18*c* has a cut-out 18*e* having a width of about 200 micrometers.

Figure 8:
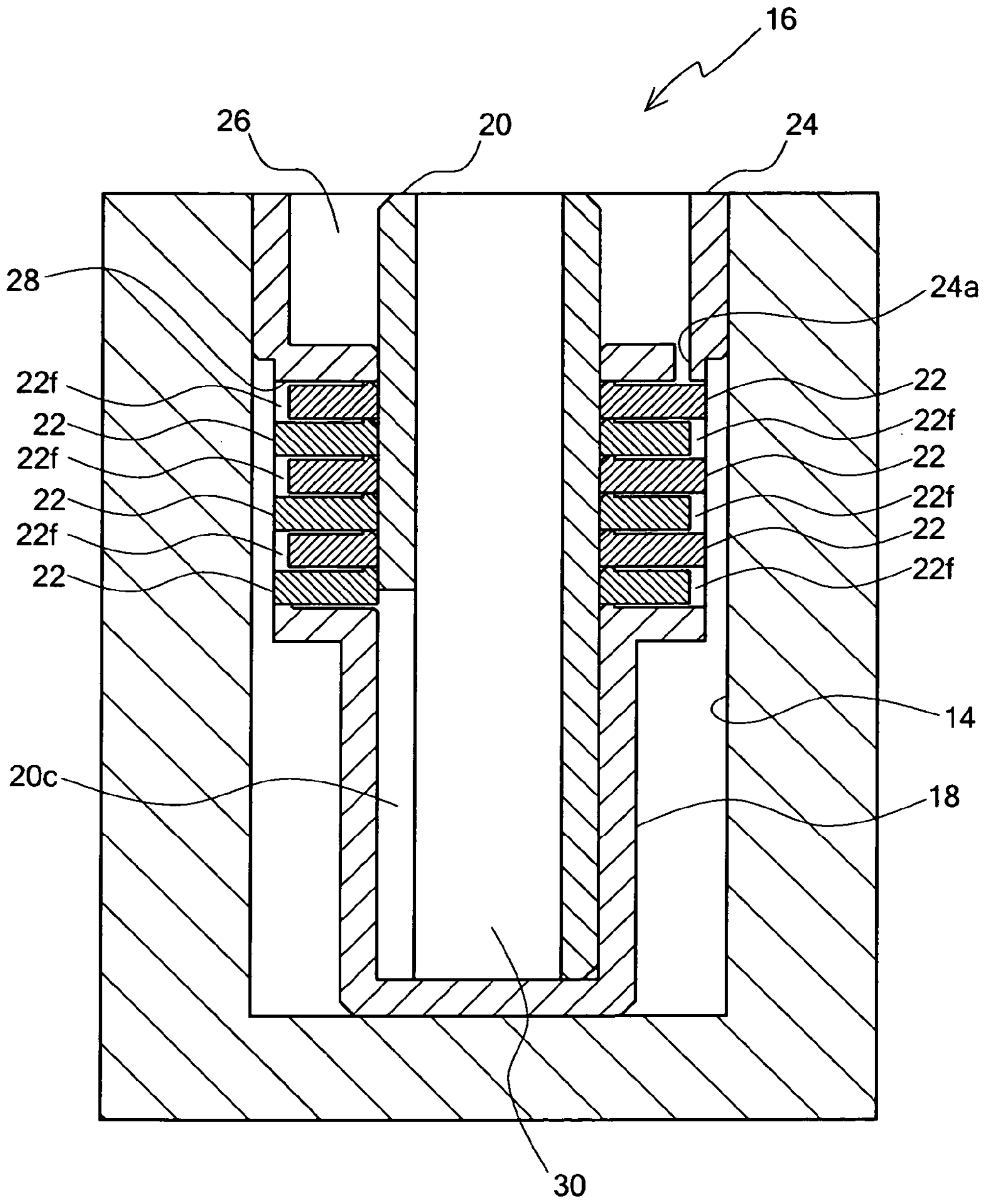
FIG. 8 is a sectional view of a modified example of a fluid handling subassembly which is mounted in each of mounting recessed portions of the first preferred embodiment of a fluid handling apparatus according to the present invention, which corresponds to FIG. 3.
Figure 9A:
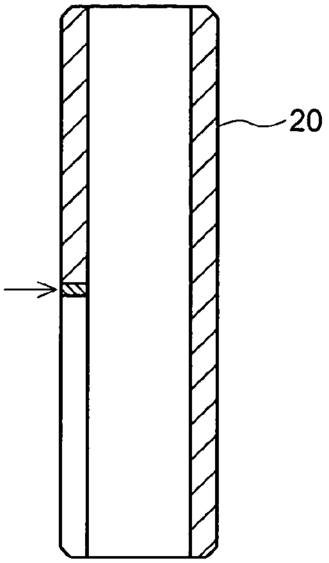
FIGS. 9A through 9E are illustrations schematically showing the flow of a fluid which flows into the interior of the inner cylindrical member of the fluid handling subassembly of FIG. 2.
Figure 9B:
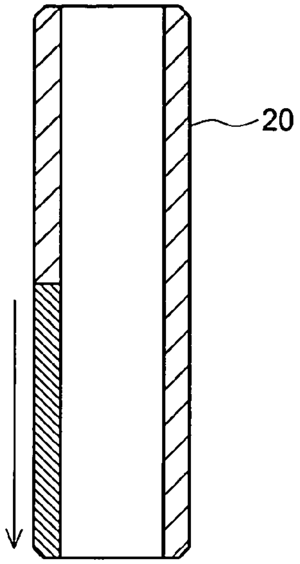
Figure 9C:
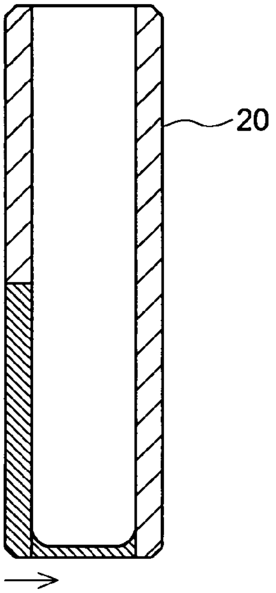
Figure 9D:
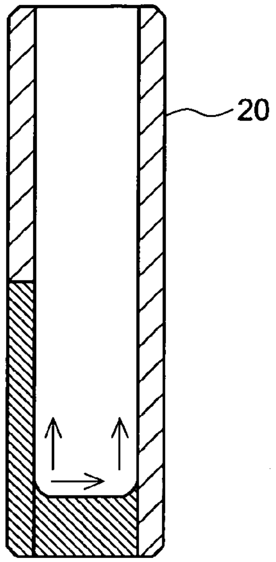
Figure 9E:
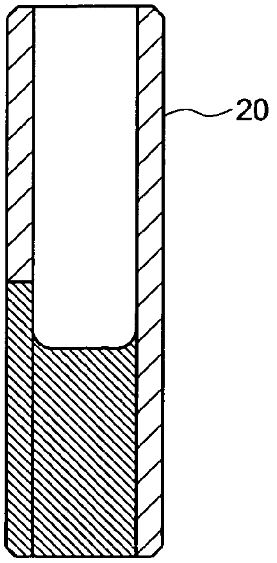

The length of the inner cylindrical member 20 is about twice the length of the outer cylindrical member 18 (the inner cylindrical member 20 has such a length that the level of the upper end of the inner cylindrical member 20 is substantially equal to that of the lid member 24 when the fluid handling subassembly 16 is assembled as shown in FIG. 3). The outside diameter of the inner cylindrical member 20 is substantially equal to the inside diameter of the outer cylindrical member 18, so that a substantially lower half of the inner cylindrical member 20 is fitted into the outer cylindrical member 18. The outer peripheral surface of the inner cylindrical member 20 has a groove 20*a* which extends in a longitudinal direction to the lower end portion. The length of the groove 20*a* is about half the length of the inner cylindrical member 20 (the groove 20*a* has such a length that the upper end of the groove 20*a* is higher than the upper surface of the flange portion 18*b* of the outer cylindrical member 18 when the inner cylindrical member 20 is fitted into the outer cylindrical member 18). The groove 20*a* has a width and depth of a few micrometers to 100 micrometers, preferably about 50 micrometers. The lower end of the groove 20*a* has a cut-out 20*b*. Furthermore, as shown in FIG. 8, a slit 20*c* having a width of a few micrometers to 100 micrometers, preferably about 50 micrometers, may be formed so as to pass through the inner cylindrical member 20 in place of the groove 20*a* and cut-out 20*b*.

As shown in FIGS. 3, 4, 6 and 7, each of the plurality of disks 22 has the same shape, and comprises: an annular disk body 22*b* having a substantially circular opening 22*a* in its central portion, into which the inner cylindrical member 20 is fitted; and an annular wall portion 22*c* which extends along the outer periphery of the disk body 22*b* in circumferential directions and protrudes upwards in a substantially vertical direction and which has a height of a few micrometers to 100 micrometers, preferably a height of about 50 micrometers, the annular wall portion 22*c* defining an annular recessed portion 22*d* on the upper surface of the disk body 22*b*. The outside diameter of each of the disks 22 is substantially equal to the outside diameter of the flange portion 18*b* of the outer cylindrical member 18, and is smaller than the inside diameter of the mounting recessed portion 14 (see FIG. 3). The annular wall portion 22*c* has a cut-out 22*e* having a width of about 200 micrometers, and a slit 22*f* on the opposite side to the cut-out 22*e* in a radial direction, the slit 22*f* having a width of about 200 micrometers. The slit 22*f* extends over the overall height of the annular wall portion 22*c*, and extends so as to cut out the peripheral portion of the disk body 22*b*. As shown in FIGS. 3, 4 and 6, the disks 22 are arranged so as to be opposed to adjacent one of the disks 22 in radial directions (arranged so as to rotate by 180 degrees with respect to adjacent one of the disks 22 in a circumferential direction about the center of the circle of each of the disks 22), and stacked so that the cut-outs 22*e* and the slits 22*f* are alternatively arranged. Furthermore, one side or both sides of each of the disks 22 may have fine irregularities.

As shown in FIGS. 3, 4 and 6, the central portion of the bottom of the lid member 24 has a substantially circular opening, into which the inner cylindrical member 20 is fitted, and the upper end of the lid member 24 has a substantially circular opening. The bottom of the lid member 24 has an opening 24*a* serving as an inlet in the vicinity of the outer periphery of the bottom of the lid member 24. The outside diameter of the lid member 24 is slightly larger than the outside diameter of the disk 22, and is substantially equal to the inside diameter of the mounting recessed portion 14.

In order to assemble the fluid handling subassembly 16 with this construction, the lower portion of the inner cylindrical member 20 is first fitted into the outer cylindrical member 18, and the lower end thereof is fixed to the bottom surface of the outer cylindrical member 18 with an adhesive or the like. Then, a plurality of disks 22 are stacked on the flange portion 18*b* of the outer cylindrical member 18 so that the cut-out 22*e* and the slits 22*f* are alternatively arranged, and the inner surface of the opening 22*a* of each of the disks 22 is fixed to the inner cylindrical member 20 with an adhesive or the like. Then, the lid member 24 is arranged over the disks 22, and the inner surface of the opening formed in the central portion of the bottom of the lid member 24 is fixed to the inner cylindrical member 20 with an adhesive or the like. The fluid handling subassembly 16 thus assembled is fitted into the mounting recessed portion 14 to be mounted therein.

If the fluid handling subassembly 16 is thus mounted in the mounting recessed portion 14, a substantially annular space serving as an injecting section 26 for injecting a fluid, such as a liquid sample, is formed by the lid member 24 and the inner cylindrical member 20. Below the injecting section 26, a fluidized section 28, which is a substantially annular space capable of being used as a reaction section in which the plurality of disks 22 are housed, is formed by the lid member 24, the inner cylindrical member 20 and the outer cylindrical member 18. The fluidized section 28 is communicated with the injecting section 26 via the opening 24*a* of the lid member 24 serving as an inlet. In the inner cylindrical member 20, there is formed a fluid housing chamber 30 which is a substantially annular space capable of being used as a measuring section.

In the fluidized section 28, substantially annular spaces are defined between the bottom surface of the lid member 24 and the uppermost disk 22, between adjacent two of the disks 22 and between the lowermost disk 22 and the flange portion 18*b* of the outer cylindrical member 18. The height of each of the substantially annular spaces is preferably set so as to allow a fluid to flow due to capillarity in view of the wettability of the fluid to the material of the disks 22. Similarly, the size of the cut-out 18*e* of the annular wall portion 18*c* of the outer cylindrical member 18, the sizes of the groove 20*a* and cut-out 20*b* (or slit 20*c*) of the inner cylindrical member 20, and the sizes of the cut-out 22*e* and slit 22*f* of the disk 22 are preferably set so as to allow a fluid to flow due to capillarity in view of the wettability of the fluid to the material thereof. If they are thus set, a fluid injected into the fluidized section 28 from the opening 24*a* of the lid member 24 serving as the inlet flows from the vicinity of the cut-out 22*e* of the uppermost disk 22 toward the slit 22*f* due to capillarity as shown by arrow in FIG. 7, and then, passes through the slit 22*f* to flow to the cut-out 22*e* of the second disk 22 below the uppermost disk 22. Then, the fluid flows toward the slit 22*f* due to capillarity. Similarly, the fluid sequentially flows on each of the disks 22 below the second disk 22. Then, after the fluid flows to the cut-out 18*e* of the annular wall portion 18*c* of the outer cylindrical member 18, the fluid flows through a passage which is formed between the inner surface of the outer cylindrical member 18 and the groove 20*a* of the inner cylindrical member 20. Then, the fluid passes through the cut-out 20*b* of the lower end of the inner cylindrical member 20 to be fed into the interior of the inner cylindrical member 20 (the fluid housing chamber 30) (see FIGS. 9A through 9E). Furthermore, if the outside diameter of each of the disks 22 is smaller than the inside diameter of the housing recessed portion 14 to form a substantially annular space outside of the disks 22, a surface tension can prevent the fluid from leaking out downwards without passing on each of the disks 22.

If the plurality of disks 22 are thus arranged in the fluidized section 28, it is possible to increase the surface area of the inner surface of the passage in the fluidized section 28. Thus, if the fluid handling apparatus 10 is used as a sample analyzing apparatus, it is possible to increase the surface area of a supporting surface (a reaction surface) for a capturing material to increase the contact area with the fluid. If a liquid is allowed to continuously flow on the large reaction surface, it is possible to enhance the efficiency of reaction, and it is possible to shorten the reaction time and improve the sensitivity of measurement, so that it is possible to reduce the quantity of used regents to reduce costs.

That is, the reaction section (fluidized section 28) and the measuring section (fluid housing chamber 30) are separately provided in the well (mounting recessed portion 14) to increase the surface area of the reaction surface in the reaction section. Thus, a small amount of liquid injected from the injecting section 26 can continuously flow in the reaction section mainly due to capillarity without the need of any external power, and it is possible to increase the distance at which the liquid moves on the reaction surface in the reaction section, so that it is possible to greatly increase the efficiency of reaction to greatly shorten the reaction time. In addition, the surface area of the reaction surface can be very large, so that it is possible to improve the sensitivity of measurement. Moreover, the reaction solution passing through the reaction section is collected in the central measuring section. Since the diameter of the measuring section is smaller than the diameter of the well, it is possible to raise the liquid level using a small amount of liquid, so that it is possible to decrease the quantity of used reagents to reduce costs.

Second Preferred Embodiment

The second preferred embodiment of a fluid handling apparatus according to the present invention will be described below. The fluid handling apparatus 110 in this preferred embodiment is substantially the same as the fluid handling apparatus 10 in the first preferred embodiment shown in FIG. 1, except that fluid handling subassemblies 116 are used in place of the fluid handling subassemblies 16. Therefore, the same reference numbers are given to the same portions, and the descriptions thereof are omitted. Furthermore, in each of the fluid handling subassemblies 116, a fluidized section 128 is filled with fine particles, such as a large number of substantially spherical fine beads 112, in place of the plurality of disks 22 in each of the fluid handling subassemblies 16.

Figure 10:
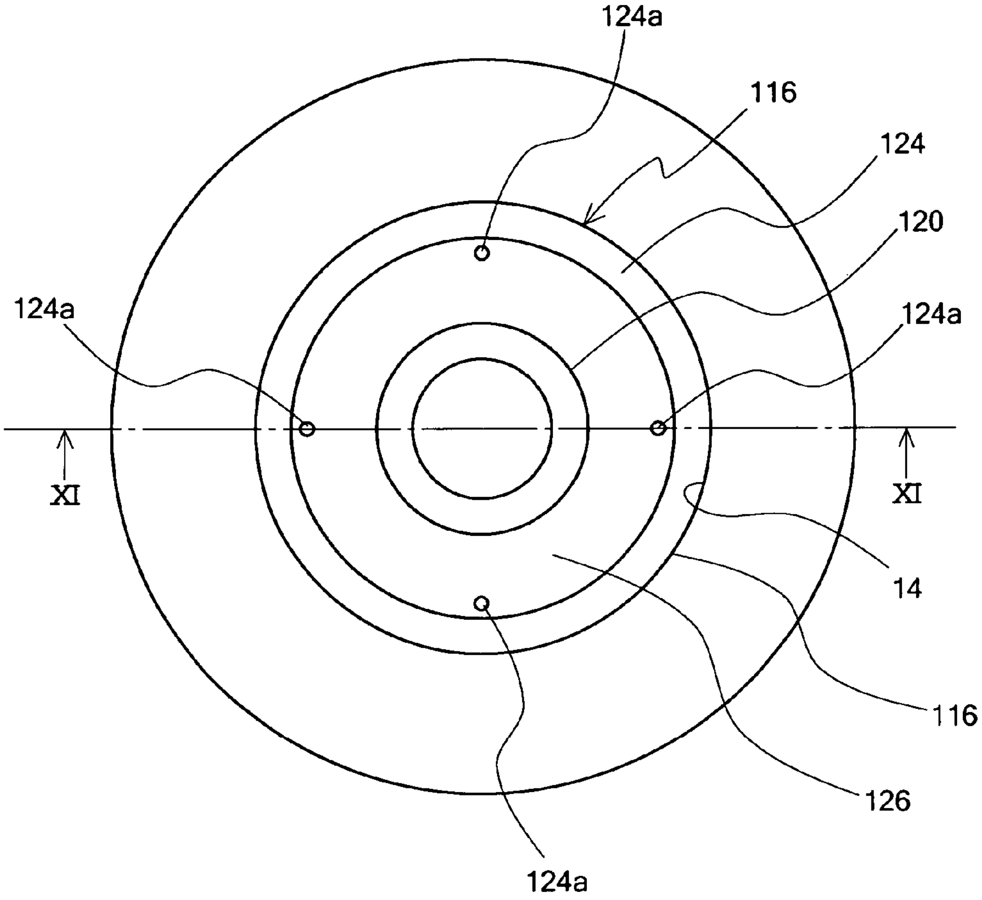
FIG. 10 is an enlarged plan view showing a fluid handling subassembly which is mounted in each of mounting recessed portions of the second preferred embodiment of a fluid handling apparatus according to the present invention.
Figure 11:
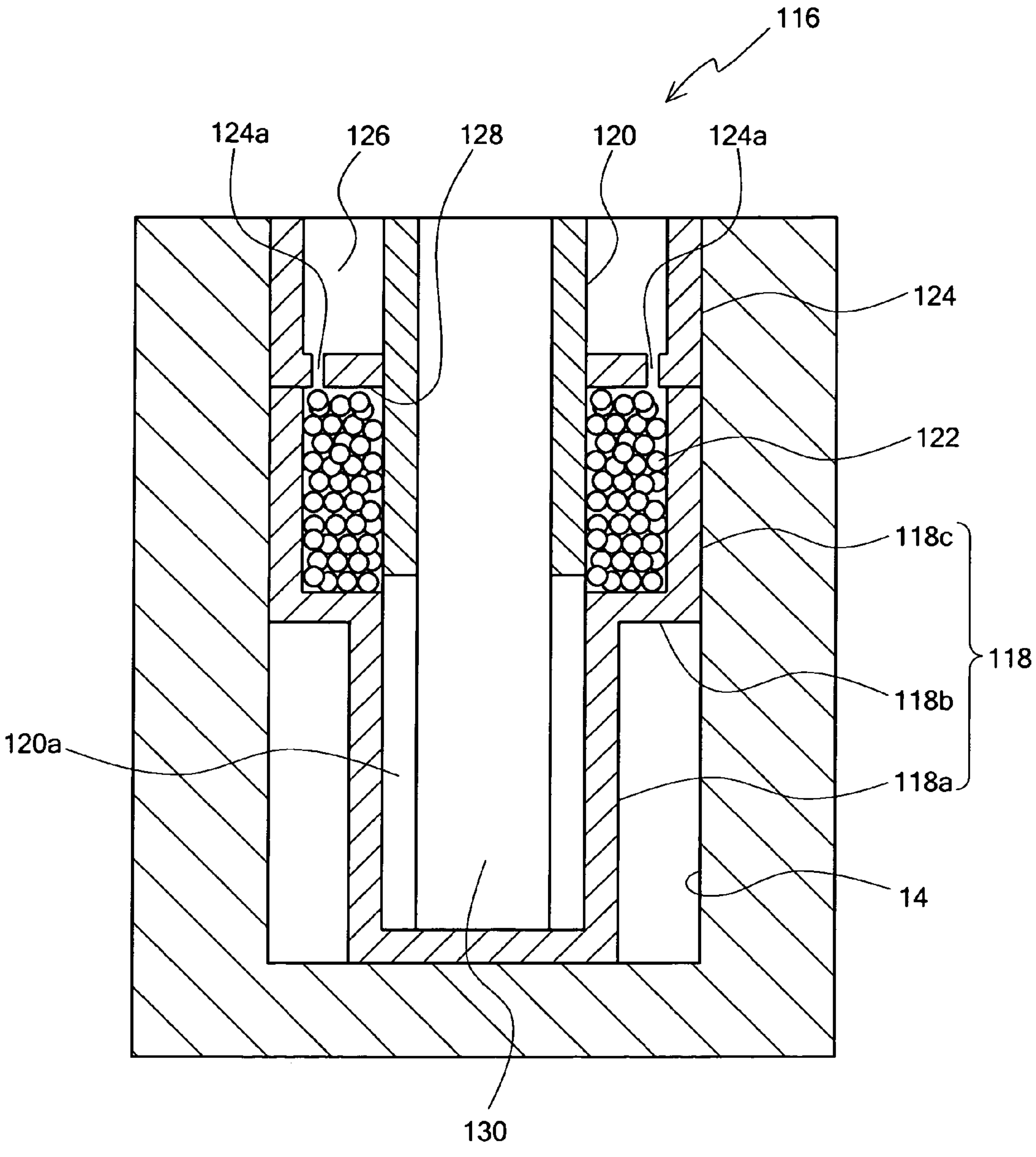
FIG. 11 is a sectional view taken along line XI-XI of FIG. 10.
Figure 12:
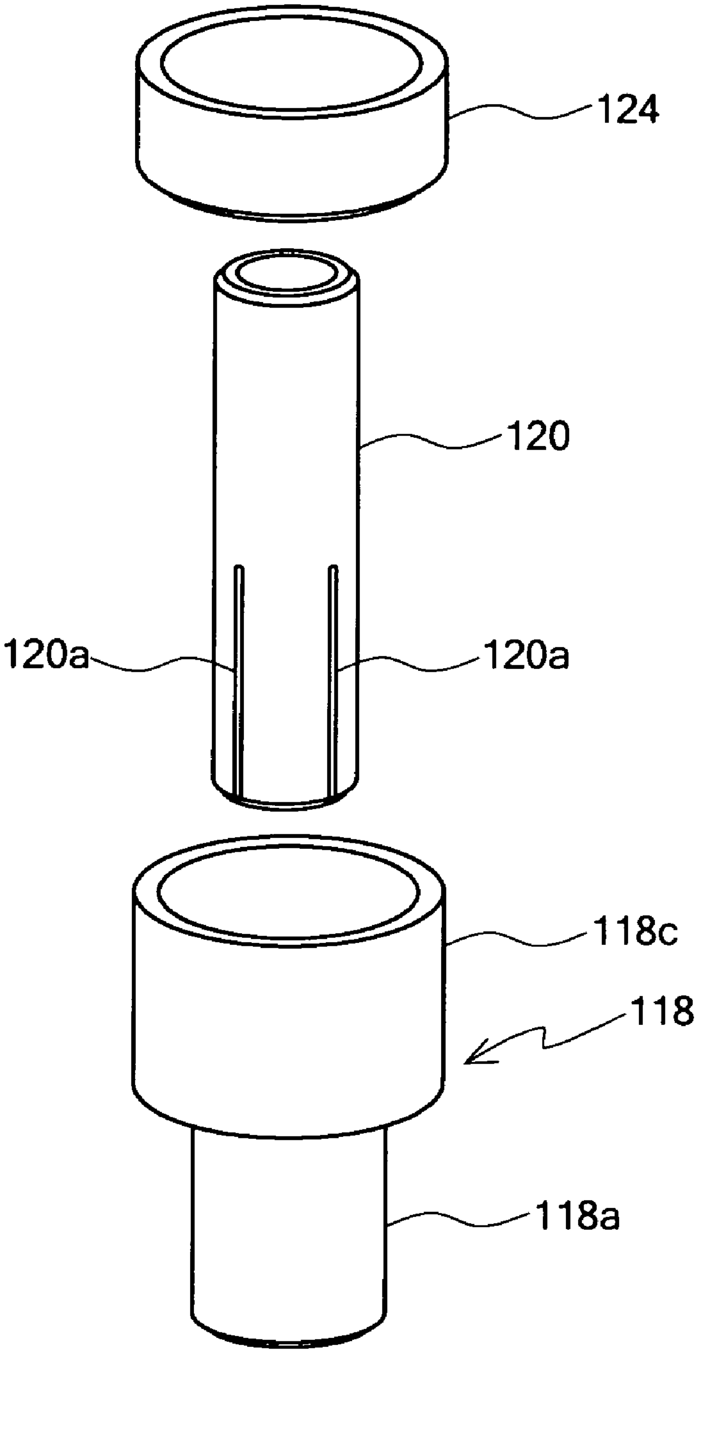
FIG. 12 is an exploded perspective view showing the fluid handling subassembly of FIG. 10, except for beads.
Figure 13:
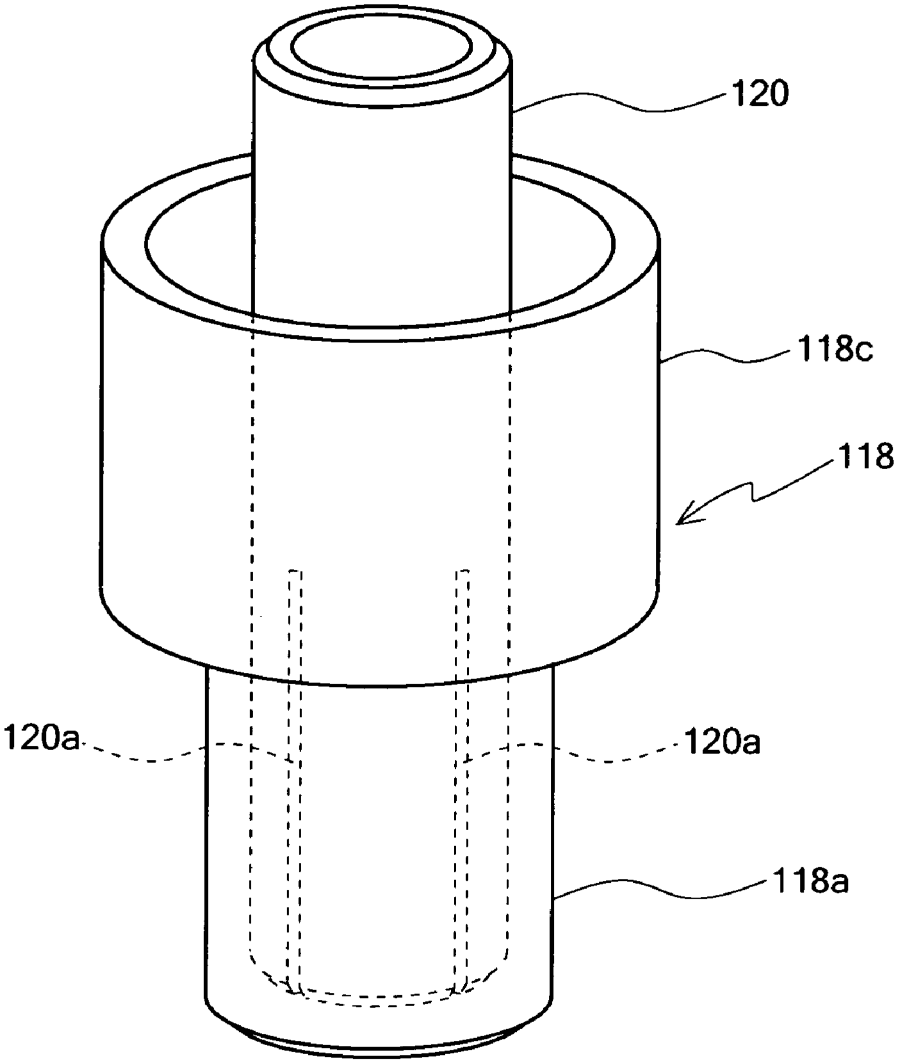
FIG. 13 is a perspective view showing a state that an inner cylindrical member of the fluid handling subassembly of FIG. 10 is inserted into an outer cylindrical member thereof.
Figure 14:
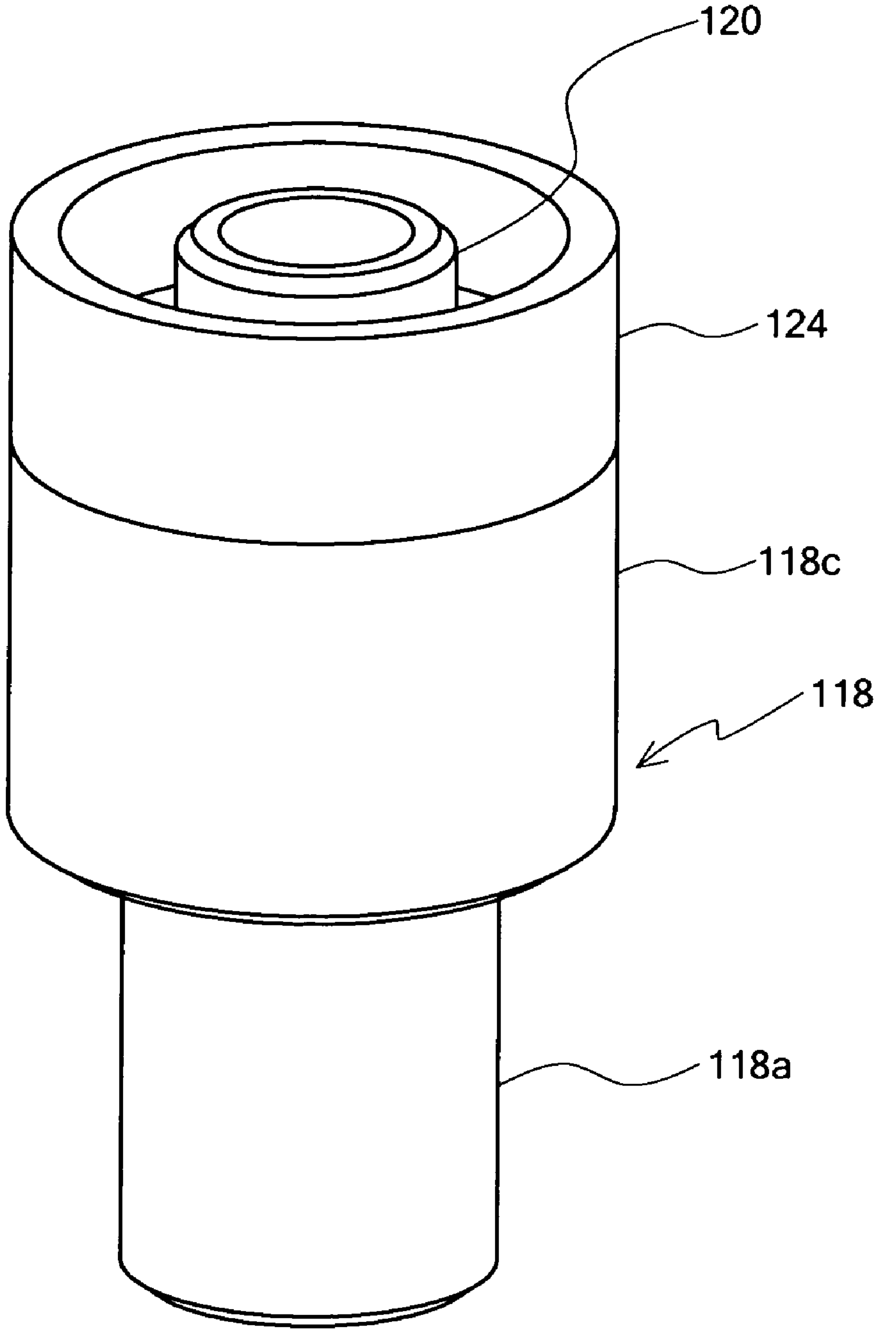
FIG. 14 is a perspective view showing a state that the fluid handling subassembly of FIG. 10 is assembled.

FIGS. 10 through 14 are enlarged views showing a fluid handling subassembly 116 which is mounted in each of the mounting recessed portions 14 of the fluid handling apparatus 110 in this preferred embodiment. FIG. 10 is a plan view of the fluid handling subassembly 116, and FIG. 11 is a sectional view taken along line XI-XI of FIG. 10. FIG. 12 is an exploded perspective view of the fluid handling subassembly 116 (except for beads 122), FIG. 13 is a perspective view showing a state that an inner cylindrical member 120 of the fluid handling subassembly 116 is inserted into an outer cylindrical member 118 thereof, and FIG. 14 is a perspective view showing a state that the fluid handling subassembly 116 is assembled.

As shown in FIGS. 10 through 14, each of the fluid handling subassemblies 116 comprises an outer cylindrical member 118 having a substantially cylindrical shape, an inner cylindrical member 120 having a substantially cylindrical shape, a large number of beads 122, and a substantially cylindrical lid member 124.

The outer cylindrical member 118 comprises: a substantially cylindrical small-diameter portion 118*a* having a diameter and height of a few millimeters; an annular portion 118*b* protruding from the upper end portion of the small-diameter portion 118*a* outwardly in substantially horizontal directions; and a substantially cylindrical large-diameter portion 118*c* which extends from the outer periphery of the annular portion 118*b* in circumferential directions and which extends upwards in a substantially vertical direction, the large-diameter portion 118*a* having a height of a few millimeters and an outside diameter which is substantially equal to the inside diameter of the mounting recessed portion 14. The lower end of the small-diameter 118*a* is closed by its bottom, and the upper end of the large-diameter portion 118*c* has a substantially circular opening.

The inner cylindrical member 120 has such a length that the level of the upper end of the inner cylindrical member 120 is substantially equal to that of the lid member 124 when the fluid handling subassembly 116 is assembled as shown in FIG. 11. The inner cylindrical member 120 has an outside diameter which is substantially equal to the inside diameter of the small-diameter portion 118*a* of the outer cylindrical member 118, so that the inner cylindrical member 120 is fitted into the small-diameter portion 118*a* of the outer cylindrical member 118. The outer peripheral surface of the inner cylindrical member 120 has a plurality of slits 120*a* (four slits 120*a* are provided in this preferred embodiment, and only two slits 120*a* are shown in FIG. 11) which extend in longitudinal directions to the lower end portion and which pass through the inner cylindrical member 120. Each of the slits 120*a* has a length which is about half the length of the inner cylindrical member 120 (each of the slits 120*a* has such a length that the upper end of the slit 120*a* is higher than the upper surface of the annular portion 118*b* of the outer cylindrical member 118 when the inner cylindrical member 120 is fitted into the outer cylindrical member 118). Each of the slits 120*a* has a width of a few micrometers to 1 millimeter, preferably about 50 micrometers. The width of each of the slits 120*a* is preferably set so as to allow a fluid to flow due to capillarity in view of the wettability of the fluid to the material of the inner cylindrical member 120.

The central portion of the bottom of the lid member 124 has a substantially circular opening, into which the inner cylindrical member 120 is fitted, and the upper end of the lid member 124 has a substantially circular opening. The bottom of the lid member 124 has a plurality of openings 124*a* serving as inlets in the vicinity of the outer periphery of the bottom of the lid member 124 (four openings 124*a* are provided in this preferred embodiment, and only two openings 124*a* are shown in FIG. 11). The outside diameter of the lid member 124 is substantially equal to the outside diameter of the large-diameter portion 118*c* of the outer cylindrical member 118, and is substantially equal to the inside diameter of the mounting recessed portion 14.

In order to assemble the fluid handling subassembly 116 with this construction, the lower portion of the inner cylindrical member 120 is first fitted into the small-diameter portion 118*a* of the outer cylindrical member 118, and the lower end thereof is fixed to the bottom surface of the outer cylindrical member 118 with an adhesive or the like. Then, a large number of beads 122 are filled in an annular space between the large-diameter portion 118*c* of the outer cylindrical member 118 and the inner cylindrical member 120. Then, the lid member 124 is arranged on the large-diameter portion 118*c* of the outer cylindrical member 118 to be fixed thereto with an adhesive or the like. The fluid handling subassembly 116 thus assembled is fitted into the mounting recessed portion 14 to be mounted therein.

If the fluid handling subassembly 116 is thus mounted in the mounting recessed portion 14, a substantially annular space serving as an injecting section 126 for injecting a fluid, such as a liquid sample, is formed by the lid member 124 and the inner cylindrical member 120. Below the injecting section 126, a fluidized section 128, which is a substantially annular space capable of being used as a reaction section filled with the large number of beads 122, is formed by the lid member 124, the inner cylindrical member 120 and the outer cylindrical member 118. The fluidized section 128 is communicated with the injecting section 126 via the openings 124*a* of the lid member 124 serving as inlets. In the inner cylindrical member 120, there is formed a fluid housing chamber 130 which is a substantially cylindrical space capable of being used as a measuring section.

If a fluid is injected into the fluidized section 128 from the openings 124*a* of the lid member 124 serving as the inlets, the fluid flows downwards in the fluidized section 128 filled with the large number of beads 122, and then, passes through the slit 120*a* of the inner cylindrical member 120 to be fed into the interior of the inner cylindrical member 120 (the fluid housing chamber 130).

If the fluidized section 128 is thus filled with the large number of beads 122, it is possible to increase the surface area of the inner surface of the passage in the fluidized section 128. Thus, if the fluid handling apparatus 110 is used as a sample analyzing apparatus, it is possible to increase the surface area of a supporting surface (a reaction surface) for a capturing material to increase the contact area with the fluid. If a liquid is allowed to continuously flow on the large reaction surface, it is possible to enhance the efficiency of reaction, and it is possible to shorten the reaction time and improve the sensitivity of measurement, so that it is possible to reduce the quantity of used regents to reduce costs.

Third Preferred Embodiment

The third preferred embodiment of a fluid handling apparatus according to the present invention will be described below. The fluid handling apparatus 210 in this preferred embodiment is substantially the same as the fluid handling apparatus 110 in the second preferred embodiment shown in FIG. 1, except that fluid handling subassemblies 216 are used in place of the fluid handling subassemblies 116. Therefore, the same reference numbers are given to the same portions, and the descriptions thereof are omitted. Furthermore, in each of the fluid handling subassemblies 216, a water absorptive member 222 is arranged in a fluidized section 228 in place of the large number of beads 212 in each of the fluid handling subassemblies 116, and the lid member 124 is not provided.

Figure 15:
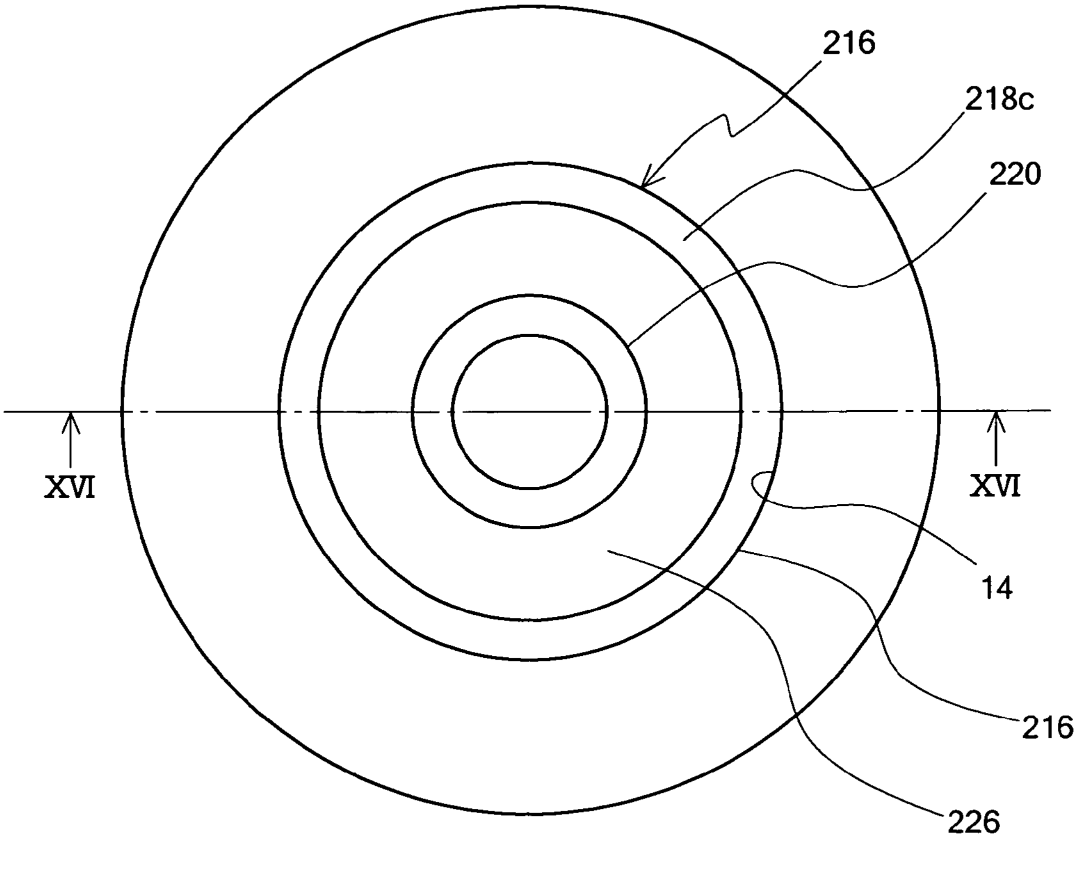
FIG. 15 is an enlarged plan view of a fluid handling subassembly which is mounted in each of mounting recessed portions of the third preferred embodiment of a fluid handling apparatus according to the present invention.
Figure 16:
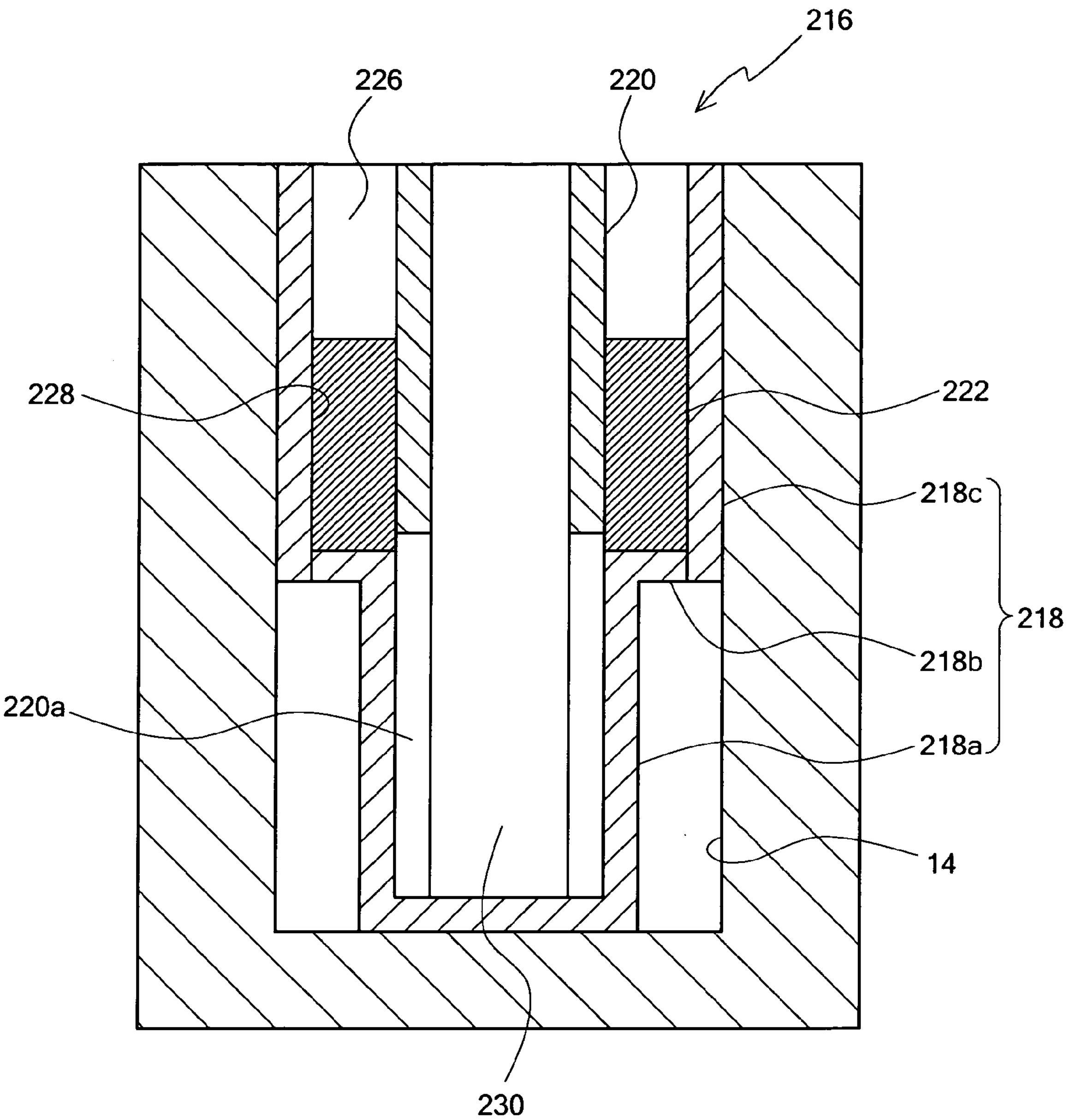
FIG. 16 is a sectional view taken along line XVI-XVI of FIG. 15.
Figure 17:
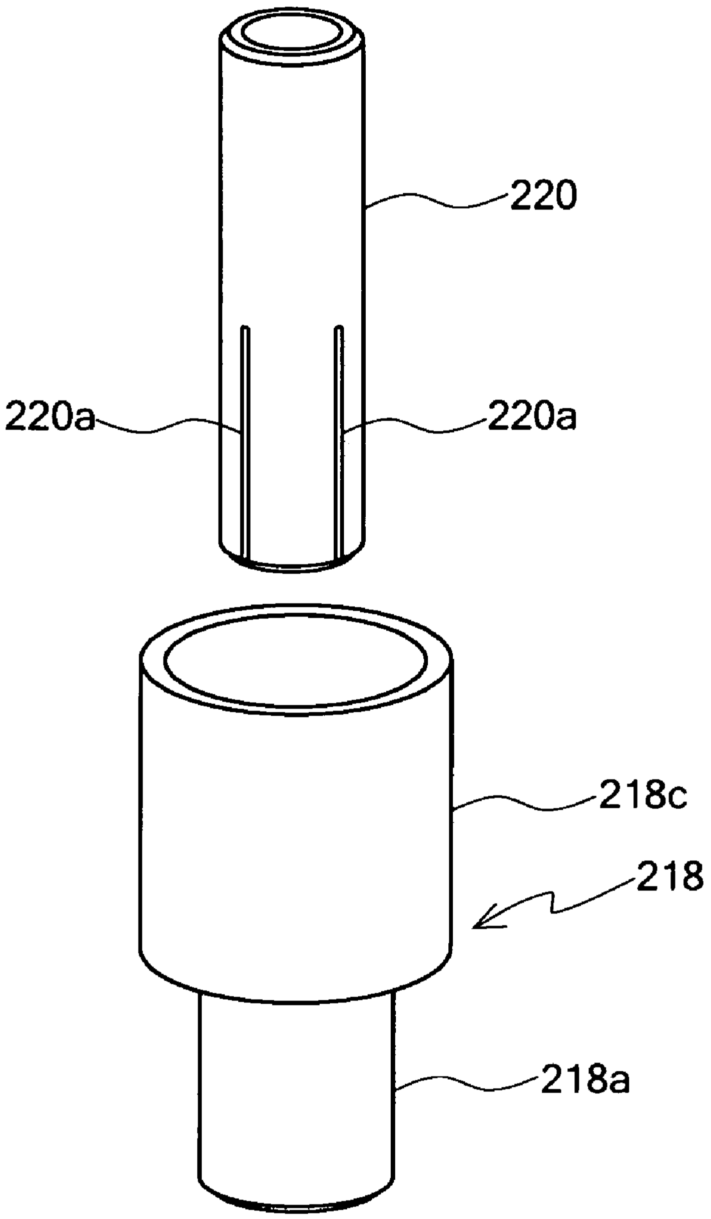
FIG. 17 is an exploded perspective view showing the fluid handling subassembly of FIG. 15, except for a water absorptive member.
Figure 18:
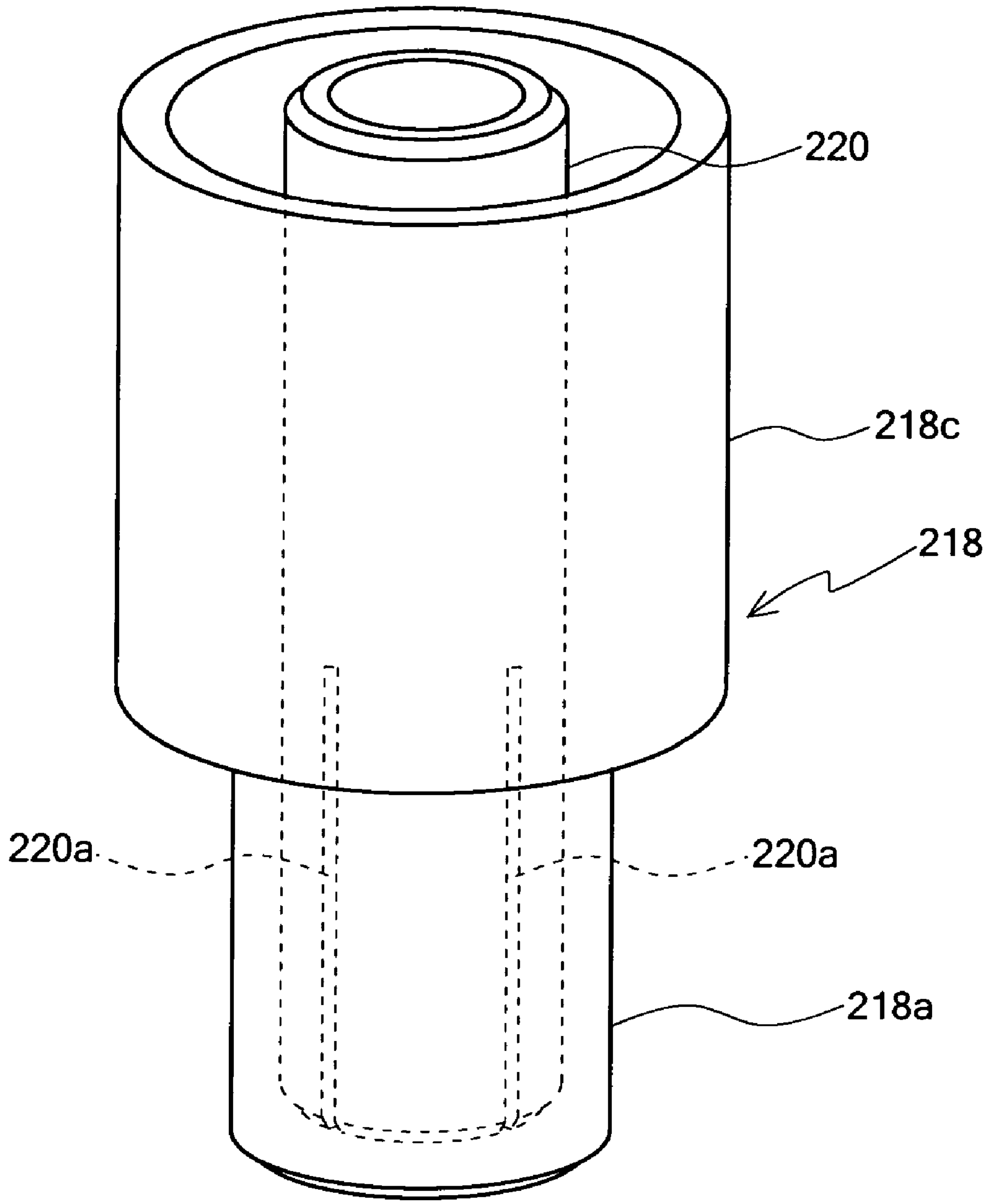
FIG. 18 is a perspective view showing a state that the fluid handling subassembly of FIG. 15 is assembled.
Figure 19:
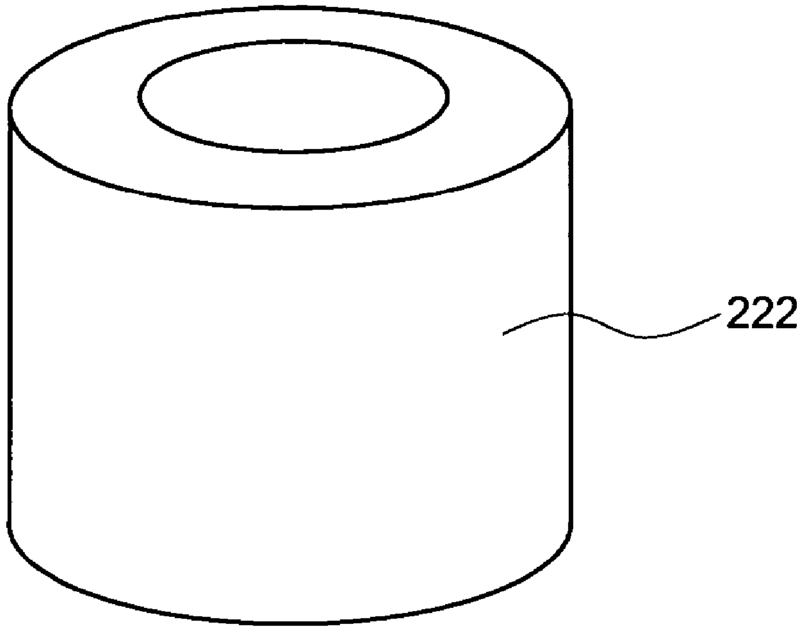
FIG. 19 is a perspective view of a water absorptive member of the fluid handling subassembly of FIG. 15.

FIGS. 15 through 19 are enlarged views showing a fluid handling subassembly 216 which is mounted in each of the mounting recessed portions 14 of the fluid handling apparatus 210 in this preferred embodiment. FIG. 15 is a plan view of the fluid handling subassembly 216, and FIG. 16 is a sectional view taken along line XVI-XVI of FIG. 15. FIG. 17 is an exploded perspective view of the fluid handling subassembly 216 (except for the water absorptive member 222), FIG. 18 is a perspective view showing a state that the fluid handling subassembly 216 is assembled, and FIG. 19 is a perspective view of the water absorptive member 222.

As shown in FIGS. 15 through 19, each of the fluid handling subassemblies 216 comprises an outer cylindrical member 218 having a substantially cylindrical shape, an inner cylindrical member 220 having a substantially cylindrical shape, and a water absorptive member 222.

The outer cylindrical member 218 comprises: a substantially cylindrical small-diameter portion 218*a* having a diameter and height of a few millimeters; an annular portion 218*b* protruding from the upper end portion of the small-diameter portion 218*a* outwardly in substantially horizontal directions; and a substantially cylindrical large-diameter portion 218*c* which extends from the outer periphery of the annular portion 218*b* in circumferential directions and which extends upwards in a substantially vertical direction, the large-diameter portion 218*a* having a height of a few millimeters and an outside diameter which is substantially equal to the inside diameter of the mounting recessed portion 14. The height of the large-diameter portion 218*c* is the sum of the height of the large-diameter portion 118*c* and the height of the lid member 124 in the second preferred embodiment. The lower end of the small-diameter 218*a* is closed by its bottom, and the upper end of the large-diameter portion 218*c* has a substantially circular opening.

The inner cylindrical member 220 has such a length that the level of the upper end of the inner cylindrical member 220 is substantially equal to that of the outer cylindrical member 218 when the fluid handling subassembly 216 is assembled as shown in FIG. 16. The inner cylindrical member 220 has an outside diameter which is substantially equal to the inside diameter of the small-diameter portion 218*a* of the outer cylindrical member 218, so that the inner cylindrical member 220 is fitted into the small-diameter portion 218*a* of the outer cylindrical member 218. The outer peripheral surface of the inner cylindrical member 220 has a plurality of slits 220*a* (four slits 220*a* are provided in this preferred embodiment, and only two slits 220*a* are shown in FIG. 16) which extend in longitudinal directions to the lower end portion and which pass through the inner cylindrical member 220. Each of the slits 220*a* has a length which is about half the length of the inner cylindrical member 220 (each of the slits 220*a* has such a length that the upper end of the slit 220*a* is higher than the upper surface of the annular portion 218*b* of the outer cylindrical member 218 when the inner cylindrical member 220 is fitted into the outer cylindrical member 218). Each of the slits 220*a* has a width of a few micrometers to 1 millimeter, preferably about 50 micrometers. The width of each of the slits 220*a* is preferably set so as to allow a fluid to flow due to capillarity in view of the wettability of the fluid to the material of the inner cylindrical member 220.

In order to assemble the fluid handling subassembly 216 with this construction, the lower portion of the inner cylindrical member 220 is first fitted into the small-diameter portion 218*a* of the outer cylindrical member 218, and the lower end thereof is fixed to the bottom surface of the outer cylindrical member 218 with an adhesive or the like. Then, the annular water absorptive member 222 is inserted into an annular space between the large-diameter portion 218*c* of the outer cylindrical member 218 and the inner cylindrical member 220. As shown in FIGS. 16 and 19, the water absorptive member 222 has an inside diameter and outer diameter which are substantially equal to those of the annular space between the large-diameter portion 218*c* of the outer cylindrical member 218 and the inner cylindrical member 220, respectively, and has a height which is lower than that of the annular space. The water absorptive member 222 is made of a material having a high water absorbing power, such as a sponge or a fiber cloth. The fluid handling subassembly 216 thus assembled is fitted into the mounting recessed portion 14 to be mounted therein.

If the fluid handling subassembly 216 is thus mounted in the mounting recessed portion 14, a substantially annular space serving as an injecting section 226 for injecting a fluid, such as a liquid sample, is formed over the water absorptive member 222. Below the injecting section 226, there is formed a fluidized section 228 which is a substantially annular space capable of being used as a reaction section in which the water absorptive member 222 is arranged. In the inner cylindrical member 220, there is formed a fluid housing chamber 230 which is a substantially cylindrical space capable of being used as a measuring section.

If a fluid is injected into the fluidized section 228 from the injecting section 226, the fluid flows downwards in the fluidized section 228 in which the water absorptive member 222 is arranged, and then, passes through the slit 220*a* of the inner cylindrical member 220 to be fed into the interior of the inner cylindrical member 220 (the fluid housing chamber 230).

If the water absorptive member 222 is thus arranged in the fluidized section 228, it is possible to increase the surface area of the inner surface of the passage in the fluidized section 228. Thus, if the fluid handling apparatus 210 is used as a sample analyzing apparatus, it is possible to increase the surface area of a supporting surface (a reaction surface) for a capturing material to increase the contact area with the fluid. If a liquid is allowed to continuously flow on the large reaction surface, it is possible to enhance the efficiency of reaction, and it is possible to shorten the reaction time and improve the sensitivity of measurement, so that it is possible to reduce the quantity of used regents to reduce costs. In particular, as compared with the above described first and second preferred embodiments, it is possible to reduce the number of parts, so that it is possible to improve productivity.

As described above, if the fluid handling apparatus 10, 110 or 210 in anyone of the first through third preferred embodiments is used as a sample analyzing apparatus, the plurality of disks 22 arranged in the fluidized section 28, the large number of fine particles (beads 122) filled in the fluidized section 128, or the water absorptive member 222 arranged in the fluidized section 228, can increase the surface area of the supporting surface (reaction surface) for the capturing material, and a reaction reagent can flow in a fine space in the fluidized section 28, 128 or 228, so that it is possible to improve the efficiency of reaction.

The reaction section (fluidized section 28, 128 or 228) and the measuring section (fluid housing chamber 30, 130 or 230) are separately provided in the well (mounting recessed portion 14). In addition, the disks 22, the fine particles (beads 122) or the water absorptive member 222 is tightly arranged in the reaction section. Thus, a small amount of liquid injected from the injecting section 26, 126 or 226 can continuously flow in the reaction section without the need of any external power, so that it is possible to greatly increase the efficiency of reaction to greatly shorten the reaction time. In addition, the surface area of the reaction surface can be very large, so that it is possible to improve the sensitivity of measurement. Moreover, the reaction solution passing through the reaction section is collected in the central measuring section. Since the diameter of the measuring section is smaller than the diameter of the well, it is possible to raise the liquid level using a small amount of liquid, so that it is possible to decrease the quantity of used reagents to reduce costs. Furthermore, if the inside diameter of the measuring section (the inside diameter of the inner cylindrical member 20, 120 or 220) is decreased so as to be substantially equal to a spot diameter of measuring light, it is possible to decrease the area of a portion, which is not measured, to further reduce the quantity of reagents to be used.

While the fluid handling subassembly 16, 116 or 216 has been mounted in each of the mounting recessed portions 14 of the plate body 12 in the fluid handling apparatus 10, 110 or 210 in any one of the above described first through third preferred embodiments, the fluid handling subassemblies 16, 116 or 216 may be mounted on a flat plate body, which has no mounting recessed portions 14, in the fluid handling apparatus according to the present invention.

While the plurality of fluid handling subassemblies 16, 116 or 216 have been separately mounted in the mounting recessed portions 14 of the plate body 12, respectively, in the fluid handling apparatus 10, 110 or 210 in any one of the above described first through third preferred embodiment, the fluid handling subassemblies 16, 116 or 216 may be integrally formed with each other or connected to each other to be mounted in the mounting recessed portions 14 of the plate body 12. For example, the lid members 24 or 124 of the fluid handling subassemblies 16 or 116 may be integrally formed with each other as one lid member in any one of the above described first and second preferred embodiments. In this case, the inner cylindrical members 20 or 120 may be integrally formed with the integrally formed lid member.

In the fluid handling apparatus 10, 110 or 210 in any one of the above described first through third preferred embodiments, one or some or part of the components of each of the fluid handling subassemblies 16, 116 or 216 may be integrally formed with the plate body 12 as long as their functions can be maintained. For example, the outer cylindrical members 18, 118 or 218 may be integrally formed with the plate body 12. In this case, the bottoms of the mounting recessed portions 14 of the plate body 12 may be used as the bottoms of the outer cylindrical members 18, 118 or 218 without providing the bottoms of the outer cylindrical members 18, 118 or 218. Alternatively, the shape of each of the mounting recessed portions 14 of the plate body 12 may be formed so as to correspond to that of each of the outer cylindrical members 18, 118 or 218, to omit the outer cylindrical members 18, 118 or 218.

When the inside diameter of the fluid housing chamber 30, 130 or 230 is large in the fluid handling apparatus 10, 110 or 210 in any one of the above described first through third preferred embodiments, if a liquid is fed into the fluid housing chamber 30, 130 or 230 so that the liquid level of the liquid fed into the fluid housing chamber 30, 130 or 230 is higher than the bottom of the fluidized section 28, 128 or 228, the liquid level of the liquid in the fluid housing chamber 30, 130 or 230 is equal to the liquid level of the liquid in the fluidized section 28, 128 or 228. However, if the inside diameter of the fluid housing chamber 30, 130 or 230 is decreased so as to cause attraction due to capillarity in view of the lyophilic of the inner wall surface of the fluid housing chamber 30, 130 or 230 with the liquid fed into the fluid housing chamber 30, 130 or 230, the total amount of fluid in the fluidized section 28, 128 or 228 can be fed into the fluid housing chamber 30, 130 or 230. If the inside diameter of the fluid housing chamber 30, 130 or 230 is thus designed so as to be small, it is possible to improve the efficiency of movement of the liquid from the fluidized section 28, 128 or 228 to the fluid housing chamber 30, 130 or 230, so that it is possible to improve the efficiency of reaction. In addition, it is possible to increase the liquid level of the liquid in the fluid housing chamber 30, 130 or 230, so that it is possible to improve the sensitivity of measurement.

Fourth Preferred Embodiment

Figure 20:
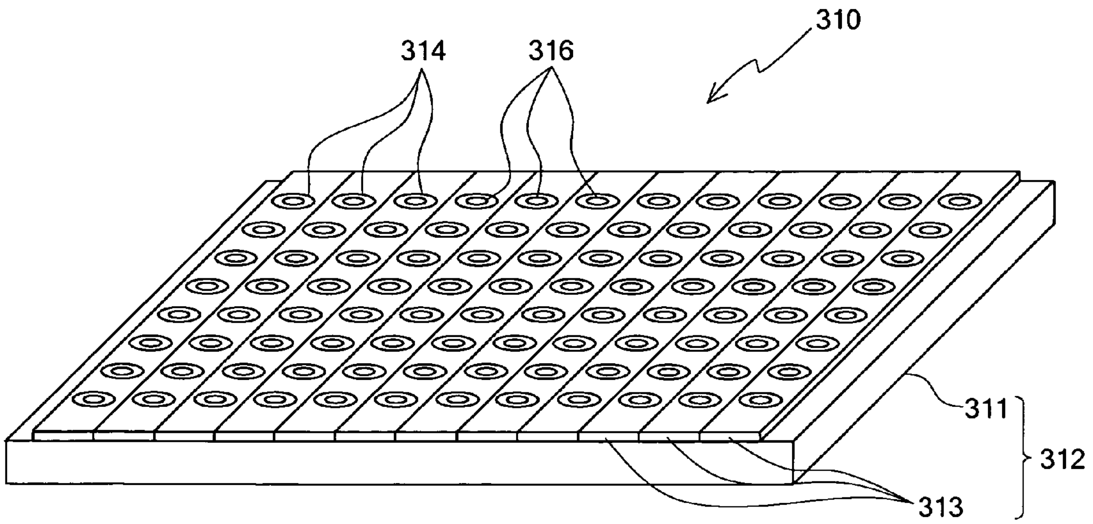
FIG. 20 is a perspective view of the fourth preferred embodiment of a fluid handling apparatus according to the present invention.

FIGS. 20 through 26 show the fourth preferred embodiment of a fluid handling apparatus according to the present invention. For example, the fluid handling apparatus 310 in this preferred embodiment similar to the above described first through third preferred embodiments can be used as an apparatus for analyzing a sample containing a biosubstance, such as a protein, which is representative of functional substances. In general, the fluid handling apparatus 310 can be used as a sample analyzing apparatus called a microwell plate for carrying out the measurement of a large number of specimens. As shown in FIG. 20, the fluid handling apparatus 310 comprises an apparatus body 312, and a plurality of fluid handling subassemblies 316 (96 fluid handling subassemblies arrayed as 8×12 in this preferred embodiment) which are mounted on the apparatus body 312.

Figure 21:
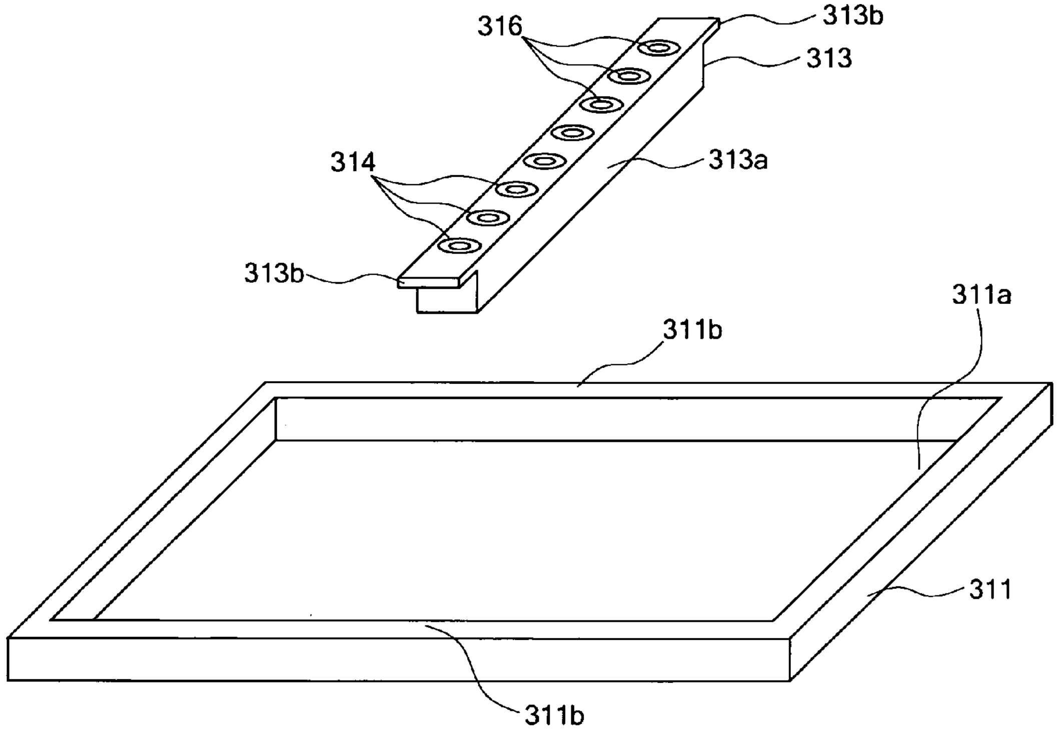
FIG. 21 is a perspective view showing a frame and a fluid handling subassembly supporting member of the fluid handling apparatus of FIG. 20.

The apparatus body 312 is made of a resin material, such as polycarbonate (PC) or polymethyl methacrylate (PMMA), or a glass material. As shown in FIGS. 20 and 21, the apparatus body 312 comprises: a substantially rectangular frame 311 which has a substantially rectangular opening 311*a* in its central portion and which has a thickness of a few millimeters and a length and width of a few centimeters to over ten centimeters; and a plurality of fluid handling subassembly supporting members 313 (12 fluid handling subassembly supporting members 313 in this preferred embodiment) which are mounted on the frame 313. The opening 311*a* of the frame 311 may be a through opening or a recessed portion with a bottom. The frame 311 may be a standard frame, such as a frame for SBS (Society for Biomolecular Screening) standard microplate. The fluid handling subassembly supporting member 313 may be made of a transparent material. However, if the fluid handling apparatus 310 in this preferred embodiment is used for measuring fluorescence, the fluid handling subassembly supporting member 313 is preferably made of a material (e.g., a black member), in which it is difficult for light to pass, in order to inhibit background from rising during the measurement of fluorescence.

As shown in FIG. 21, each of the fluid handling subassembly supporting members 313 comprises: an elongated supporting member body 313*a* having a shape of substantially rectangular parallelopiped, the supporting member body 313*a* having a length which is substantially equal to the width of the opening 311*a* of the frame 311; and a pair of substantially rectangular protruding portions 313*b* which protrude from both ends of the upper portion of the supporting member body 313*a* in longitudinal directions and which extend along the upper surface of the supporting member body 313*a*. As shown in FIG. 20, the supporting member body 313*a* of each of the fluid handling subassembly supporting members 313 is inserted into the opening 311*a* of the frame 311 to allow the fluid handling subassembly supporting members 313 to be closely mounted on the frame 311 in parallel so that the protruding portions 313_b_ of each of the fluid handling assembly supporting members 313 are supported on a pair of upper surfaces 311_b_ extending in longitudinal directions of the frame 311. Thus, the apparatus body 312 is assembled.

Figure 22:
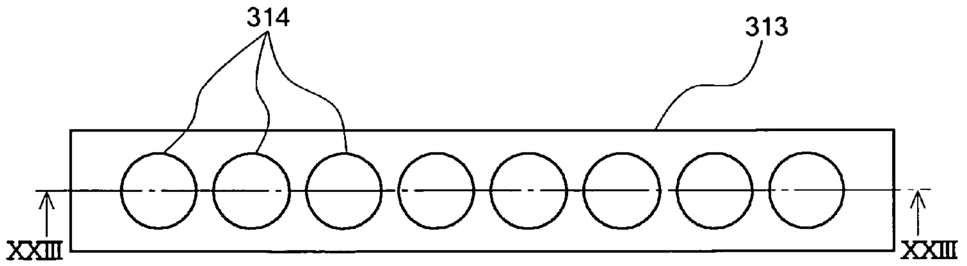
FIG. 22 is an enlarged plan view of the fluid handling subassembly supporting member of FIG. 21.
Figure 23:
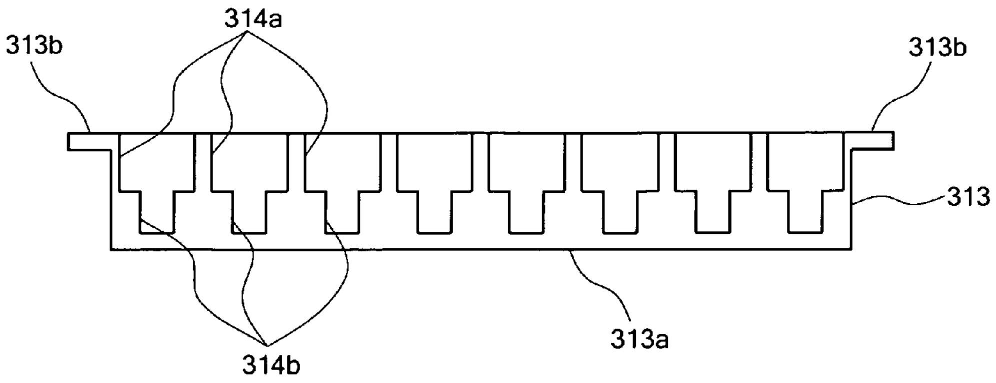
FIG. 23 is a sectional view taken along line XXIII-XXIII of FIG. 22.

As shown in FIGS. 20 through 22, in the upper surface of the supporting member body 313_a_ of each of the fluid handling subassembly supporting members 313, a plurality of recessed portions 314 (which will be hereinafter referred to as "mounting recessed portions 314") (eight recessed portions 314 in this preferred embodiment) are formed so as to be arranged in a row at regular intervals. Each of the mounting recessed portions 314 comprises: a substantially cylindrical large-diameter recessed portion 314_a_ which is formed in the upper surface of the supporting member body 313_a_ and which has a depth substantially half of the height of the supporting member body 313_a_; and a substantially cylindrical small-diameter recessed portion 314_a_ which is formed in a substantially central portion of the bottom of the large-diameter recessed portion 314_a_. The fluid handling subassemblies 316 are mounted in the mounting recessed portions 314, respectively.

Figure 24:
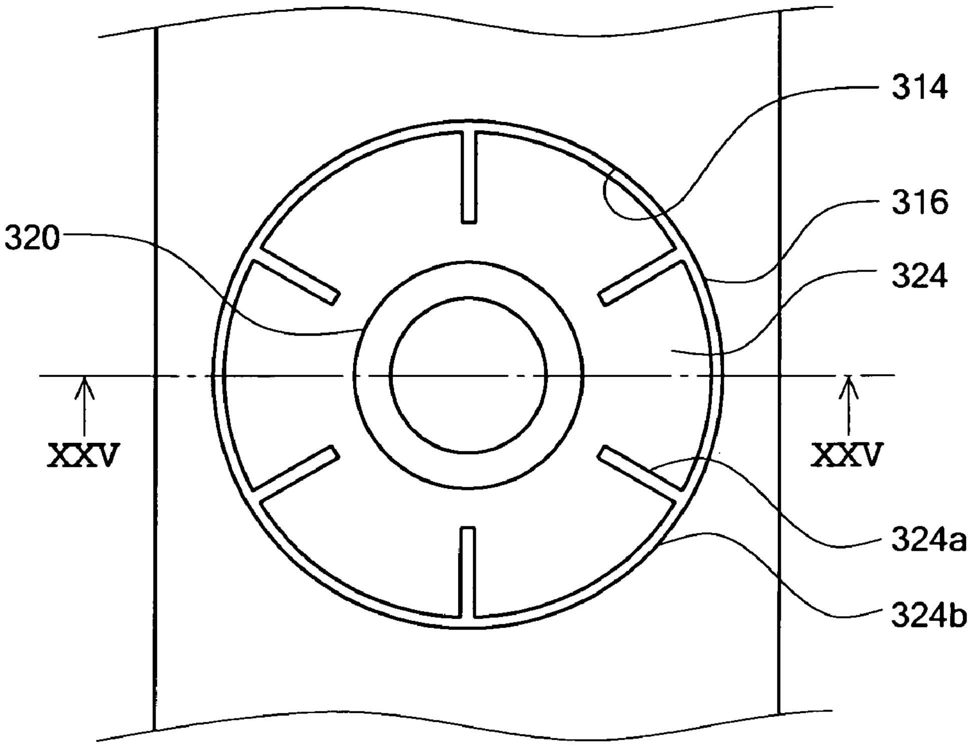
FIG. 24 is a plan view of a fluid handling subassembly of the fluid handling apparatus of FIG. 20.
Figure 25:
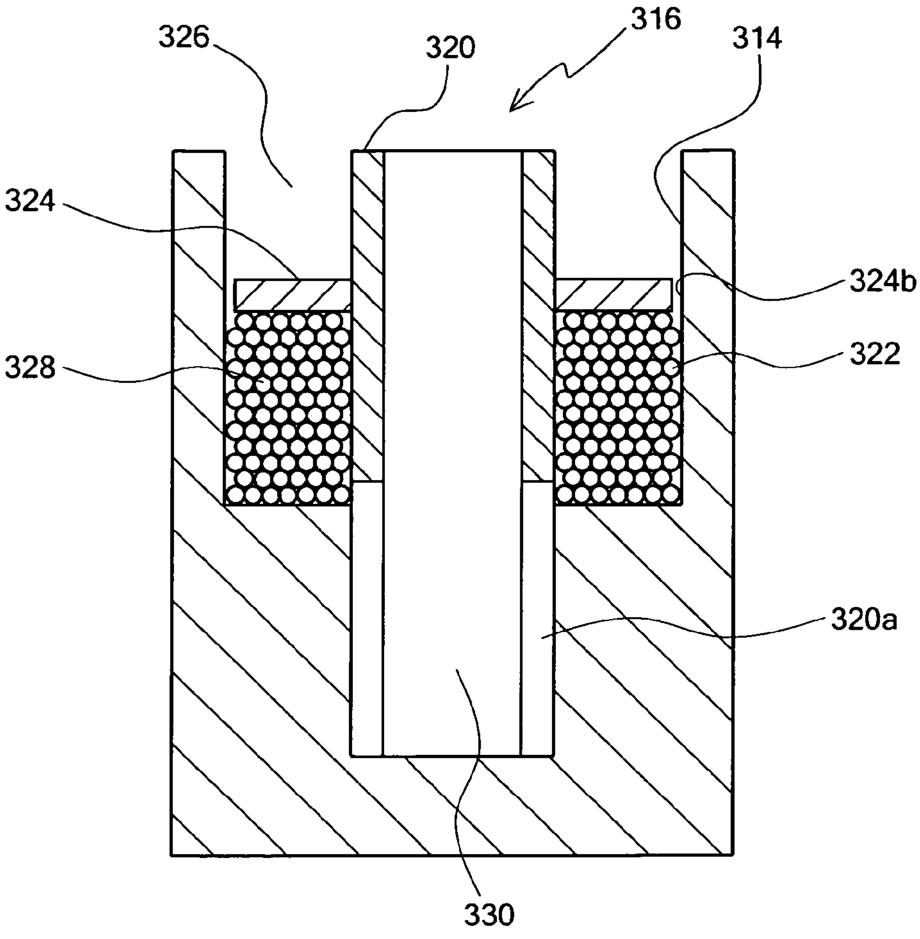
FIG. 25 is a sectional view taken along line XXV-XXV of FIG. 24.
Figure 26:
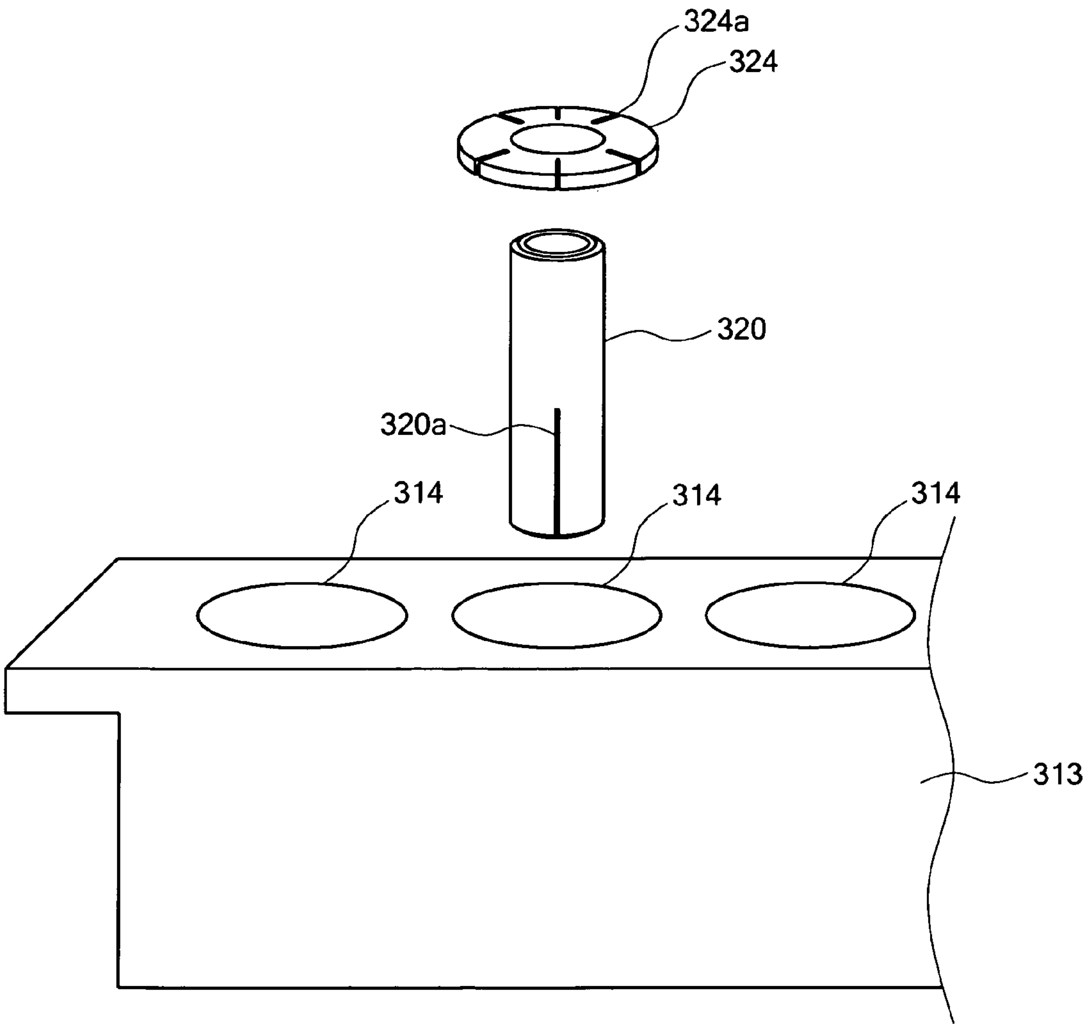
FIG. 26 is an exploded perspective view showing the fluid handling subassembly of the fluid handling apparatus of FIG. 20, except for beads.

FIGS. 24 through 26 are enlarged views showing a fluid handling subassembly 316 which is mounted in each of the mounting recessed portions 314 of the fluid handling apparatus 310 in this preferred embodiment. FIG. 24 is a plan view of the fluid handling subassembly 316 which is mounted in one of the mounting recessed portions 314 of the fluid handling apparatus 310, and FIG. 25 is a sectional view taken along line XXV-XXV of FIG. 24. FIG. 26 is an exploded perspective view of the fluid handling subassembly 316 (except for beads 322).

As shown in FIGS. 24 through 26, each of the fluid handling subassemblies 316 comprises a cylindrical member 320 which has a substantially cylindrical shape and which has a diameter and height of a few millimeters, a large number of fine beads 322 having a substantially spherical shape, and a substantially annular disk-shaped lid member 324.

As shown in FIG. 25, the cylindrical member 320 has a length which is substantially equal to the depth of the mounting recessed portion 314 (the large-diameter recessed portion 314_a_ and the small-diameter recessed portion 314_b_), and has an outside diameter which is substantially equal to the inside diameter of the small-diameter recessed portion 314_b_ of the mounting recessed portion 314, so that the cylindrical member 320 is fitted into the small-diameter recessed portion 314_b_ of the mounting recessed portion 314 (the inside diameter of the cylindrical member 320 may be, e.g., about 2.5 millimeters). The outer peripheral surface of the cylindrical member 320 has a plurality of slits 320_a_ (four slits 320_a_ are provided in this preferred embodiment, and only two slits 320_a_ are shown in FIG. 25) which extend in longitudinal directions to the lower end portion and which pass through the cylindrical member 320. Each of the slits 320_a_ has a length which is about half the length of the cylindrical member 320 (each of the slits 320_a_ has such a length that the upper end of the slit 320_a_ is higher than the bottom of the large-diameter recessed portion 314_a_ when the cylindrical member 320 is fitted into the small-diameter recessed portion 314_b_ of the mounting recessed portion 314). Each of the slits 320_a_ has a width of a few micrometers to 1 millimeter, preferably about 50 micrometers. The width of each of the slits 320_a_ is preferably set so as to allow a fluid to flow due to capillarity in view of the wettability of the fluid to the material of the cylindrical member 320.

The central portion of the lid member 324 has a substantially circular opening, into which the cylindrical member 320 is fitted. In the peripheral portion of the lid member 324, a plurality slit-shaped openings 324_a_ (six openings 324_a_ in this preferred embodiment) serving as inlets are formed so as to extend radially at regular intervals. The outside diameter of the lid member 324 is slightly smaller than the inside diameter of the large-diameter recessed portion 314_a_ of the mounting recessed portion 314, so that an annular opening 324_b_ serving as an inlet is formed between the lid member 324 and the mounting recessed portion 314 when the lid member 324 is inserted into the mounting recessed portion 314.

In order to assemble the fluid handling subassembly 316 with this construction, the lower portion of the cylindrical member 320 is first fitted into the small-diameter recessed portion 314_b_ of the mounting recessed portion 314, and the lower end thereof is fixed to the bottom surface of the small-diameter recessed portion 314_b_ of the mounting recessed portion 314 with an adhesive or the like. Then, a large number of beads 322 are filled in an annular space between the large-diameter recessed portion 314_a_ of the mounting recessed portion 314 and the cylindrical member 320. Then, the lid member 324 is fitted onto the cylindrical member 320 to be arranged on the beads 322 to be fixed thereto with an adhesive or the like.

If the fluid handling subassembly 316 is thus mounted in the mounting recessed portion 314, a substantially annular space serving as an injecting section 326 for injecting a fluid, such as a liquid sample, is formed between the large-diameter recessed portion 314_a_ of the mounting recessed portion 314 and the cylindrical member 320. Below the injecting section 326, a fluidized section 328, which is a substantially annular space capable of being used as a reaction section filled with the large number of beads 322, is formed between the large-diameter recessed portion 314_a_ of the mounting recessed portion 314 and the cylindrical member 320. The fluidized section 328 is communicated with the injecting section 326 via the openings 324_a_ and 324_b_ of the lid member 324 serving as inlets. In the inner cylindrical member 320, there is formed a fluid housing chamber 330 which is a substantially annular space capable of being used as a measuring section.

If a fluid is injected into the fluidized section 328 from the openings 324_a_ and 324_b_ of the lid member 324 serving as the inlets, the fluid flows downwards in the fluidized section 328 filled with the large number of beads 322, and then, passes through the slits 320_a_ of the cylindrical member 320 to be fed into the interior of the cylindrical member 320 (the fluid housing chamber 330).

If the fluidized section 328 is thus filled with the large number of beads 322, it is possible to increase the surface area of the inner surface of the passage in the fluidized section 328. Thus, if the fluid handling apparatus 310 is used as a sample analyzing apparatus, it is possible to increase the surface area of a supporting surface (a reaction surface) for a capturing material to increase the contact area with the fluid. If a liquid is allowed to continuously flow on the large reaction surface, it is possible to enhance the efficiency of reaction, and it is possible to shorten the reaction time and improve the sensitivity of measurement, so that it is possible to reduce the quantity of used regents to reduce costs.

In this preferred embodiment, the fluid handling subassemblies 316 are mounted on the fluid handling subassembly supporting member 313 of the apparatus body 312, so that a fluid handling unit, wherein the plurality of fluid handling subassemblies 316 are arranged in a row at regular intervals, can be mounted on the frame 311 of the apparatus body 312. Thus, the fluid handling units can be separately mounted on the frame 311 every one row, so that handling is easy. In addition, since it is not required to provide the outer cylindrical members 118 or 218 of the fluid handling apparatus 110 or 210 in the above described second or third preferred embodiment, the volume of the reaction section can be larger than that of the fluid handling apparatus 110 or 210 in any one of the second and third preferred embodiments, so that it is possible to further improve the sensitivity of measurement. In addition, the fluid handling subassembly supporting member 313 is formed of a black member in which it is difficult for light to pass, so that it is possible to inhibit background from rising during the measurement of fluorescence. Moreover, the number of parts can be smaller than that in the above described first and second preferred embodiments, so that it is possible to improve productivity.

Furthermore, each of the mounting recessed portions 314 of the fluid handling subassembly supporting members 313 of the fluid handling apparatus 310 in this preferred embodiment may have a substantially cylindrical shape to be mounted in the fluid handling subassembly 16, 116 or 216 of the fluid handling apparatus 10, 110 or 210 in any one of the above described preferred first through third preferred embodiments. If recessed portions having the same shape as the mounting recessed portion 314 (the large-diameter recessed portion 314*a* and the small-diameter recessed portion 314*b*) of the fluid handling apparatus 310 in this preferred embodiment are formed in a substantially cylindrical member, the fluid handling subassembly 316 may be mounted in each of the recessed portions thus formed, to be mounted on the plate body 12 of the fluid handling apparatus 10, 110 or 210 in the above described first through third preferred embodiments.

As examples of fluid handling apparatuses 10, 110 and 310 in the above described first, second and fourth preferred embodiments, examples of fluid handling apparatuses used as sample analyzing apparatuses will be described below.

EXAMPLE 1

The surface of each of disks 22 for a fluid handling subassembly 16 of a fluid handling apparatus 10 in the first preferred embodiment was coated with anti-human TNF-alpha antibody (500 ng/ml), which was labeled with biotin, to be allowed to stand for one night. Then, each of the disks 22 thus coated was blocked with a commercially available blocking agent. Then, the disks 22 thus processed were used for assembling a fluid handling subassembly 16 which was mounted in the mounting recessed portion 14 of the plate body 12 of a fluid handling apparatus 10.

Then, 30 μl of streptoavidin-HRP (200 ng/ml) was fed into the injecting section 26 of the fluid handling subassembly 16 to be allowed to react for 20 minutes (a period of time in which 30 μl of streptoavidin-HRP fed into the injecting section 26 was collected in the fluid housing chamber 30), and then, the interior of the fluid handling subassembly 16 was washed with 30 μl of a buffer three times.

Then, 15 μl of a substrate (a substrate of QuantaBlu (Registered Trademark) Fluorogenic Peroxidase Substrate Kit produced by Pierce Biotechnology, Inc.) was fed into the injecting section 26 to be allowed to react for 20 minutes, and then, 15 μl of a reaction stop solution (a reaction stop solution of QuantaBlu (Registered Trademark) Fluorogenic Peroxidase Substrate Kit produced by Pierce Biotechnology, Inc.) was added thereto. Then, the fluid housing chamber 30 was irradiated with excitation light having a wavelength of 325 nm in a longitudinal direction (in a vertical direction) to measure the intensity of fluorescence (the intensity of fluorescence at a wavelength of 420 nm) of a reaction solution in the fluid housing chamber 30.

COMPARATIVE EXAMPLE 1

The intensity of fluorescence was measured by the same method as that in Example 1, except that a commercially available microwell plate having 96 wells arrayed as 8×12 was used in place of the fluid handling apparatus 10, that the wall surface of one of the wells was coated with anti-human TNF-alpha antibody (500 ng/ml), which was labeled with biotin, to be blocked, that the amount of streptoavidin-HRP (200 ng/ml) was 100 μl, that the amount of the buffer for one washing was 100 μl, and that the amount of each of the substrate and the reaction stop solution was 100 μl.

Figure 27:
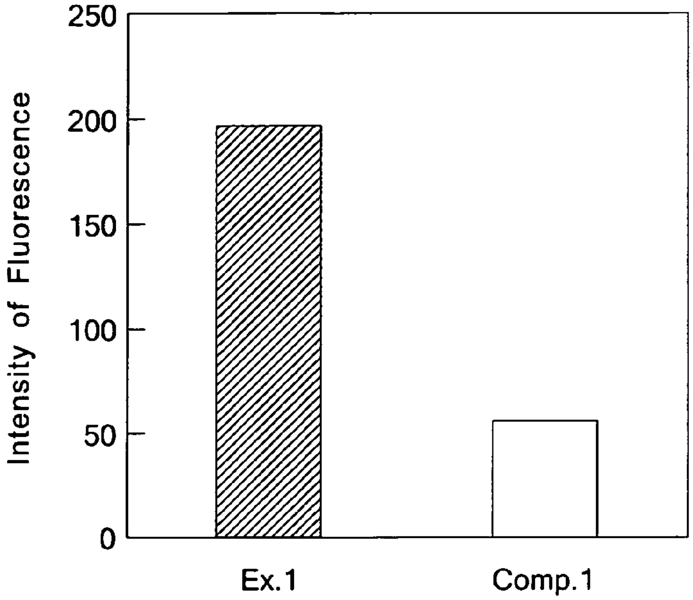
FIG. 27 is a graph showing the results of the intensity of fluorescence in Example 1 and Comparative Example 1.

From the results in Example 1 and Comparative Example 1, it was found that the intensity of fluorescence (a mean value in three times) was 55.59 in Comparative Example 1, whereas the intensity of fluorescence was 195.57 to be greatly increased in Example 1, so that it was possible to greatly enhance the intensity of measurement using a small amount of liquid in Example 1 as compared with Comparative Example 1. These results are shown in FIG. 27.

EXAMPLE 2

The surface of each of beads (Production Number 4330A (particle diameter: 300 micrometers) produced by Duke Scientific) 122 for a fluid handling apparatus 110 in the second preferred embodiment was coated with anti-human TNF-alpha antibody (50 ng/ml), which was labeled with biotin, to be allowed to stand for one night. Then, each of the beads 122 thus coated was blocked with a commercially available blocking agent. Then, the beads 122 thus processed were used for assembling a fluid handling subassembly 116 which was mounted in the mounting recessed portion 14 of the plate body 12 of a fluid handling apparatus 110.

Then, 30 μl of streptoavidin-HRP (200 ng/ml) was fed into the injecting section 126 of the fluid handling subassembly 116 to be allowed to react for 2 minutes, 10 minutes and 20 minutes, respectively (streptoavidin-HRP was circulated four times in each of these periods of time, i.e., an operation for sucking a reaction solution, which was collected in the fluid housing chamber (measuring section) 130, by means of a pipette was repeated four times), and then, the interior of the fluid handling subassembly 116 was washed with 30 μl of a buffer three times.

Then, 25 μl of a substrate (a substrate of QuantaBlu (Registered Trademark) Fluorogenic Peroxidase Substrate Kit produced by Pierce Biotechnology, Inc.) was fed into the injecting section 126 to be allowed to react for 20 minutes while a liquid collected in the fluid housing chamber (measuring section) 130 was sucked to be returned to the injecting section 126 every five minutes, and then, 25 μl of a reaction stop solution (a reaction stop solution of QuantaBlu (Registered Trademark) Fluorogenic Peroxidase Substrate Kit produced by Pierce Biotechnology, Inc.) was added thereto. Then, the fluid housing chamber 130 was irradiated with excitation light having a wavelength of 325 nm in a longitudinal direction (in a vertical direction) to measure the intensity of fluorescence (the intensity of fluorescence at a wavelength of 420 nm) of a reaction solution in the fluid housing chamber 130.

COMPARATIVE EXAMPLE 2

The intensity of fluorescence was measured by the same method as that in Example 2, except that a commercially available microwell plate having 96 wells arrayed as 8×12 was used in place of the fluid handling apparatus 110, that the wall surface of one of the wells was coated with anti-human TNF-alpha antibody (50 ng/ml), which was labeled with biotin, to be blocked, that 100 μl of streptoavidin-HRP (200 ng/ml) was fed at a time, that the amount of the buffer for one washing was 100 μl, that 100 μl of the substrate was fed at a time, and that the amount of the reaction stop solution was 100 μl.

Figure 28:
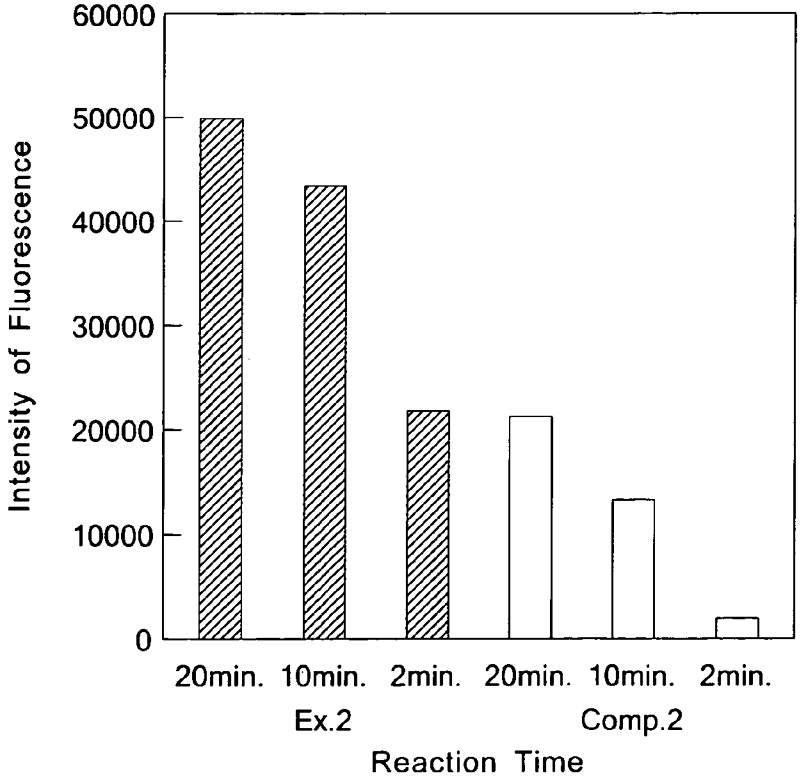
FIG. 28 is a graph showing the results of the intensity of fluorescence in Example 2 and Comparative Example 2.

From the results in Example 2 and Comparative Example 2, it was found that the intensities of fluorescence in reaction times of 2 minutes, 10 minutes and 20 minutes were 2023.0, 13404.5 and 21350.5, respectively in Comparative Example 2, whereas the intensities of fluorescence in reaction times of 2 minutes, 10 minutes and 20 minutes were 21790.0 (a mean value in twice), 43438.0 and 49914.0, respectively, to be greatly increased in Example 2, so that it was possible to greatly enhance the intensity of measurement using a small amount of liquid in Example 2 as compared with Comparative Example 2. These results are shown in FIG. 28.

Furthermore, in Example 2, even if a liquid passes through the fluidized section (reaction section) 126 filled with the beads 122, a part of a reagent remains in the reaction section. Therefore, it can be seen that, if the reaction time is increased, the remaining liquid is allowed to continuously react, so that the intensity of fluorescence is enhanced. In addition, if the sensitivity of measurement is sufficient to be usual sensitivity, the reaction time maybe about 2 minutes, so that it is possible to rapidly carry out measurement. If it is desired to carry out measurement at high sensitivity, the reaction time can be increased to measure a very small amount of sample.

EXAMPLE 3

The surface of each of beads (Production Number 7640A (mean particle diameter: 134 micrometers) produced by Duke Scientific) 322 for a fluid handling apparatus 310 in the fourth preferred embodiment was coated with anti-human TNF-alpha antibody (5 μg/ml) by means of a reagent kit (PolyLink-Protein Coupling Kit for COOH Microparticles produced by Polysciences, Inc.), to be allowed to stand for one night. Then, each of the beads 322 thus coated was blocked with a commercially available blocking agent. Then, the beads 322 thus processed were used for assembling a fluid handling subassembly 316 which was mounted in the apparatus body 312 of a fluid handling apparatus 310.

Then, 30 μl of human TNF-alpha (25 pg/ml) serving as a sample was fed into the injecting section 326 of the fluid handling subassembly 316 to be arrowed to react for one hour, and then, the interior of the fluid handling subassembly 316 was washed with 50 μl of a buffer three times.

Then, 30 μl of human TNF-alpha antibody (0.5 μg/ml) labeled with biotin was fed into the injecting section 326 to be allowed to react for one hour, and then, the interior of the fluid handling subassembly 316 was washed with 50 μl of a buffer three times.

Then, 30 μl of streptoavidin-AP (100 ng/ml) was fed into the injecting section 326 to be allowed to react for 20 minutes, and then, the interior of the fluid handling subassembly 316 was washed with 50 μl of a buffer three times.

Then, 30 μl of a substrate (a substrate of AttoPhos (Registered Trademark) AP Fluorescent Substrate System produced by Promega) was fed into the injecting section 326 to be allowed to react for 10 minutes, and then, 30 μl of a reaction stop solution (0.5 N of NaOH solution) was added thereto. Then, the fluid housing chamber 330 was irradiated with excitation light having a wavelength of 435 nm from the top in a longitudinal direction (in a vertical direction) to measure the intensity of fluorescence (the intensity of fluorescence at a wavelength of 555 nm) of a reaction solution in the fluid housing chamber 330 by means of a microplate reader.

COMPARATIVE EXAMPLE 3

The intensity of fluorescence was measured by the same method as that in Example 3, except that a commercially available microwell plate having 96 wells arrayed as 8×12 was used in place of the fluid handling apparatus 310, that the wall surface of one of the wells was coated with the same anti-human TNF-alpha antibody as that in Example 3 to be blocked, that 50 μl of human TNF-alpha (25 pg/ml) was fed as a sample at a time, that 100 μl of human TNF-alpha antibody (0.5 μg/ml) labeled with biotin was fed at a time, that 100 μl of streptoavidin-AP (100 ng/ml) was fed at a time, that the amount of the buffer for each of the washing processes was 100 μl, that 100 μl of the substrate was fed at a time, and that the amount of the reaction stop solution was 100 μl.

COMPARATIVE EXAMPLE 4

The intensity of fluorescence was measured by the same method as that in Comparative Example 3, except that 50 μl of human TNF-alpha (100 pg/ml) was used as a sample.

Figure 29:
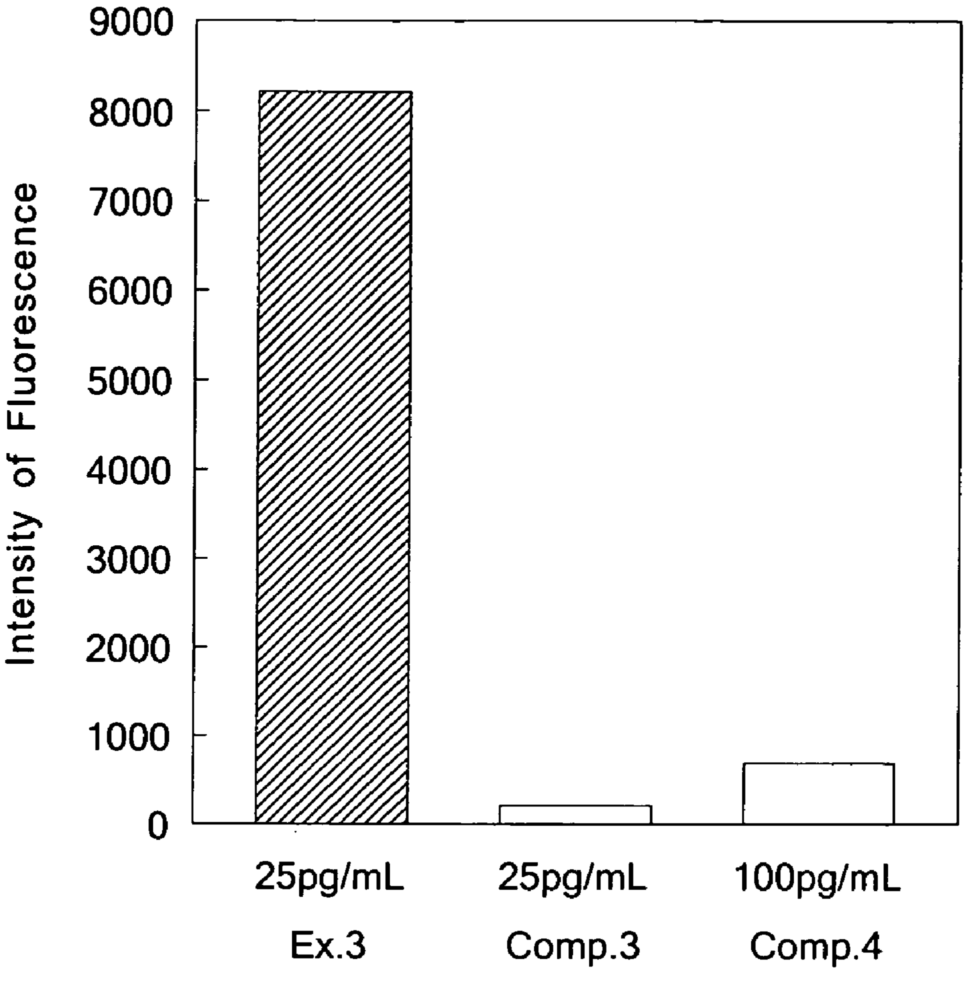
FIG. 29 is a graph showing the results of the intensity of fluorescence in Example 3 and Comparative Examples 3 and 4.

From the results in Example 3 and Comparative Examples 3 and 4, it was found that the intensity of fluorescence in Example 3 was far higher than the intensity of fluorescence in Comparative Example 3, in which the concentration of the sample was equal to that in Example 3, and than the intensity of fluorescence in Comparative Example 4 in which the concentration of the sample was four times as high as that in Example 3, so that it was possible to greatly enhance the intensity of measurement using a small amount of liquid in Example 3. These results are shown in FIG. 29.

EXAMPLE 4

The intensity of fluorescence was measured by the same method as that in Example 3, except that the concentration of the sample was 50 pg/ml and that the reaction time for the sample and the reaction time for the human TNF-alpha antibody (0.5 μg/ml) labeled with biotin were 5 minutes.

COMPARATIVE EXAMPLE 5

The intensity of fluorescence was measured by the same method as that in Comparative Example 3, except that the concentration of the sample was 50 pg/ml and that the reaction time for the sample and the reaction time for the human TNF-alpha antibody (0.5 μg/ml) labeled with biotin were 5 minutes.

COMPARATIVE EXAMPLE 6

The intensity of fluorescence was measured by the same method as that in Comparative Example 5, except that the reaction time for the sample and the reaction time for the human TNF-alpha antibody (0.5 μg/ml) labeled with biotin were 30 minutes.

COMPARATIVE EXAMPLE 7

The intensity of fluorescence was measured by the same method as that in Comparative Example 5, except that the reaction time for the sample and the reaction time for the human TNF-alpha antibody (0.5 μg/ml) labeled with biotin were 60 minutes.

Figure 30:
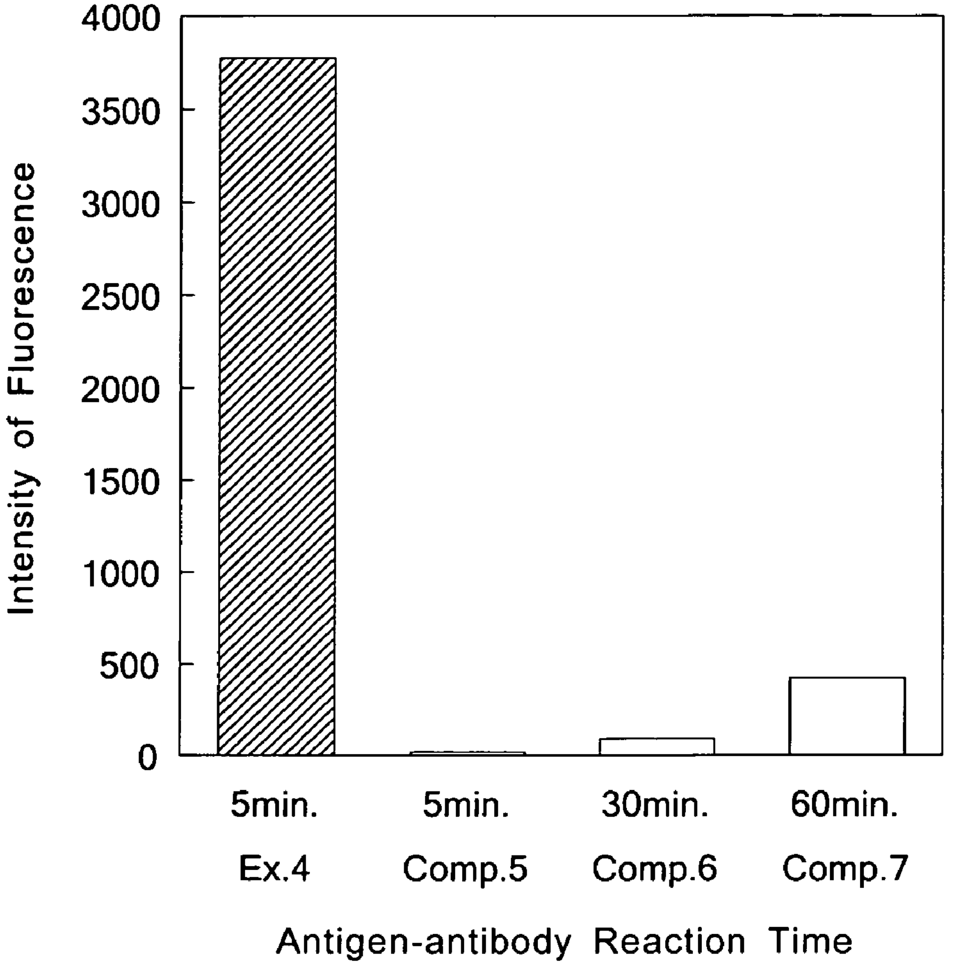
FIG. 30 is a graph showing the results of the intensity of fluorescence in Example 4 and Comparative Examples 5 through 7.

From the results in Example 4 and Comparative Examples 5 through 7, it was found that the intensity of fluorescence in Example 4 was far higher than the intensity of fluorescence in Comparative Example 5, in which the antigen-antibody reaction time was equal to that in Example 4, and than the intensity of fluorescence in Comparative Examples 6 and 7 in which the antigen-antibody reaction time was six and twelfth times as long as that in Example 4, respectively, so that it was possible to greatly enhance the intensity of measurement and greatly shorten the reaction time using a small amount of liquid in Example 4. These results are shown in FIG. 30.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A fluid handling apparatus comprising an apparatus body having a plurality of recessed portion which are formed in one surface of the apparatus body so as to be arrayed, and a plurality of fluid handling subassemblies, each of which is mounted in a corresponding one of the plurality of recessed portions, each of the fluid handling subassemblies comprising:

an injecting section for injecting a fluid, said injecting section having a bottom which has an opening;

a fluidized section for receiving the fluid from the opening of the bottom of the injecting section to allow the fluid to continuously flow downwards;

a fluid housing chamber for receiving the fluid from the fluidized section;

a fluid passage for allowing the fluid, which reaches a bottom of the fluidized section, to be fed to a lower portion of the fluid housing chamber; and a surface-area increasing means, arranged in the fluidized section, for increasing a surface area of a contact surface with the fluid in the fluidized section, wherein said injecting section and said fluidized section are arranged so as to surround said fluid housing chamber.

2. A fluid handling apparatus as set forth in claim 1, wherein said apparatus body comprises a plate member.

3. A fluid handling apparatus as set forth in claim 1, wherein said apparatus body comprises a frame and a plurality of supporting members which are arranged on the frame so as to be substantially parallel to each other, each of the supporting members having a plurality of recessed portions which are arranged in a row at regular intervals, and each of said plurality of fluid handling subassemblies being mounted in a corresponding one of the recessed portions.

4. A fluid handling apparatus as set forth in claim 1, wherein said surface-area increasing means comprises a plurality of plate members which are stacked in vertical directions to form spaces between the plate members, and the fluid fed into said fluidized section flows on an upper surface of each of the plate members.

5. A fluid handling apparatus as set forth in claim 1, wherein said surface-area increasing means comprises a large number of fine particles filled in said fluidized section.

6. A fluid handling apparatus as set forth in claim 1, wherein said surface-area increasing means is a water absorptive member arranged in said fluidized section.

7. A fluid handling apparatus as set forth in claim 1, wherein said fluid passage extends between the bottom of the fluidized section and the lower portion of the fluid housing chamber.

8. A fluid handling apparatus comprising an apparatus body and a plurality of fluid handling subassemblies arranged on the apparatus body, each of the fluid handling subassemblies comprising:

an injecting section for injecting a fluid, said injecting section having a bottom which has an opening;

a fluidized section for receiving the fluid from the opening of the bottom of the injecting section to allow the fluid to continuously flow downwards;

a fluid housing chamber for receiving the fluid from the fluidized section;

a fluid passage for allowing the fluid, which reaches a bottom of the fluidized section, to enter the fluid housing chamber; and a surface-area increasing means, arranged in the fluidized section, for increasing a surface area of a contact surface with the fluid in the fluidized section, wherein said apparatus body comprises a plate member, wherein a plurality of recessed portions are formed in one surface of said plate member so as to be arrayed, and each of said plurality of fluid handling subassemblies is mounted in a corresponding one of the recessed portions, and wherein each of said plurality of recessed portions is a substantially circular recessed portion, said fluidized section being formed between an outer cylindrical member, which is inserted into each of said plurality of recessed portions, and an inner cylindrical member which is inserted into said outer cylindrical member, said fluid housing chamber being formed in said inner cylindrical member, said surface-area increasing means comprising a plurality of circular plate members which are stacked so as to surround said inner cylindrical member, said injecting section being formed between an upper cylindrical member, which is arranged over said plurality of circular plate members, and said inner cylindrical member, a space being formed between adjacent two of said plurality of circular plate members, and the fluid fed into said fluidized section moving on an upper surface of each of said circular plate members.

9. A fluid handling apparatus as set forth in claim 8, wherein the fluid fed into said fluidized section is allowed to flow on an uppermost circular plate member of said plurality of circular plate members from a peripheral portion of the uppermost circular plate member to the opposite side in radial directions, to flow downwards in vertical directions to reach a peripheral portion of a second circular plate member of said plurality of circular plate members below the uppermost circular plate member, to sequentially flow on each of said plurality of circular plate members to reach a lowermost circular plate member of said plurality of circular plate members.

10. A fluid handling apparatus comprising an apparatus body and a plurality of fluid handling subassemblies arranged on the apparatus body, each of the fluid handling subassemblies comprising:

an injecting section for injecting a fluid, said injecting section having a bottom which has an opening;

a fluidized section for receiving the fluid from the opening of the bottom of the injecting section to allow the fluid to continuously flow downwards;

a fluid housing chamber for receiving the fluid from the fluidized section;

a fluid passage for allowing the fluid, which reaches a bottom of the fluidized section, to enter the fluid housing chamber; and a surface-area increasing means, arranged in the fluidized section, for increasing a surface area of a contact surface with the fluid in the fluidized section, wherein said apparatus body comprises a plate member, wherein a plurality of recessed portions are formed in one surface of said plate member so as to be arrayed, and each of said plurality of fluid handling subassemblies is mounted in a corresponding one of the recessed portions, and wherein each of said plurality of recessed portions is a substantially circular recessed portion, said fluidized section being formed between an outer cylindrical member, which is inserted into each of said plurality of recessed portions, and an inner cylindrical member which is inserted into said outer cylindrical member, said fluid housing chamber being formed in said inner cylindrical member, said injecting section being formed between an upper cylindrical member, which is arranged over said outer cylindrical member, and said inner cylindrical member, and said surface-area increasing means comprising a large number of fine particles filled in said fluidized section.

11. A fluid handling apparatus comprising an apparatus body and a plurality of fluid handling subassemblies arranged on the apparatus body, each of the fluid handling subassemblies comprising:

an injecting section for injecting a fluid, said injecting section having a bottom which has an opening;

a fluidized section for receiving the fluid from the opening of the bottom of the injecting section to allow the fluid to continuously flow downwards;

a fluid housing chamber for receiving the fluid from the fluidized section;

a fluid passage for allowing the fluid, which reaches a bottom of the fluidized section, to enter the fluid housing chamber; and a surface-area increasing means, arranged in the fluidized section, for increasing a surface area of a contact surface with the fluid in the fluidized section, wherein said apparatus body comprises a plate member, wherein a plurality of recessed portions are formed in one surface of said plate member so as to be arrayed, and each of said plurality of fluid handling subassemblies is mounted in a corresponding one of the recessed portions, and wherein each of said plurality of recessed portions comprises an upper cylindrical recessed portion, and a lower cylindrical recessed portion which is formed in a bottom of said upper recessed portion and which has a smaller diameter than that of said upper recessed portion, said fluidized section being formed between said upper recessed portion and a cylindrical member which is inserted into each of said plurality of recessed portions, said fluid housing chamber being formed in said cylindrical member, and said injecting section being formed over a large number of fine particles which are filled as said surface-area increasing means in said fluidized section.

12. A fluid handling apparatus comprising an apparatus body and a plurality of fluid handling subassemblies arranged on the apparatus body, each of the fluid handling subassemblies comprising:

an injecting section for injecting a fluid, said injecting section having a bottom which has an opening;

a fluidized section for receiving the fluid from the opening of the bottom of the injecting section to allow the fluid to continuously flow downwards;

a fluid housing chamber for receiving the fluid from the fluidized section;

a fluid passage for allowing the fluid, which reaches a bottom of the fluidized section, to enter the fluid housing chamber; and a surface-area increasing means, arranged in the fluidized section, for increasing a surface area of a contact surface with the fluid in the fluidized section, wherein said apparatus body comprises a plate member, wherein a plurality of recessed portions are formed in one surface of said plate member so as to be arrayed, and each of said plurality of fluid handling subassemblies is mounted in a corresponding one of the recessed portions, and wherein each of said plurality of recessed portions is a substantially circular recessed portion, said fluidized section being formed between an outer cylindrical member, which is inserted into each of said plurality of recessed portions, and an inner cylindrical member which is inserted into said outer cylindrical member, said fluid housing chamber being formed in said inner cylindrical member, and said injecting section being formed over a water absorptive member which is arranged as said surface-area increasing means in said fluidized section.

* * * * *